US007935719B2

(12) United States Patent
Solvibile et al.

(10) Patent No.: US 7,935,719 B2
(45) Date of Patent: *May 3, 2011

(54) N-SUBSTITUTED-AZACYCLYLAMINES AS HISTAMINE-3 ANTAGONISTS

(75) Inventors: William Ronald Solvibile, East Windsor, NJ (US); Ji-In Kim, Princeton, NJ (US); Marla Jean Williams, Flemington, NJ (US); Jonathan Laird Gross, Cranbury, NJ (US); Albert Jean Robichaud, Ringoes, NJ (US)

(73) Assignee: Wyeth LLC, Madison, NJ (US)

( * ) Notice: Subject to any disclaimer, the term of this patent is extended or adjusted under 35 U.S.C. 154(b) by 600 days.

This patent is subject to a terminal disclaimer.

(21) Appl. No.: 11/867,830

(22) Filed: Oct. 5, 2007

(65) Prior Publication Data

US 2008/0119458 A1 May 22, 2008

Related U.S. Application Data

(60) Provisional application No. 60/850,143, filed on Oct. 6, 2006.

(51) Int. Cl.
A61K 31/4184 (2006.01)
C07D 403/02 (2006.01)

(52) U.S. Cl. .................. 514/394; 548/301.7; 548/304.7; 548/306.1; 544/358; 544/370; 546/184; 546/199; 514/315; 514/322; 514/385

(58) Field of Classification Search ............... 548/301.7, 548/302.7, 304.7, 306.1; 546/184, 195, 199; 544/358, 359, 370; 514/315, 322, 385, 394
See application file for complete search history.

(56) References Cited

U.S. PATENT DOCUMENTS

| 3,933,829 | A | 1/1976 | Archibald et al. |
| 4,159,331 | A | 6/1979 | McCall |
| 4,166,853 | A | 9/1979 | McCall |
| 5,883,096 | A | 3/1999 | Lowe et al. |
| 6,541,499 | B1 | 4/2003 | Bastian et al. |
| 2005/0256102 | A1 | 11/2005 | Claiborne et al. |
| 2006/0014733 | A1 | 1/2006 | Howard, Jr. et al. |
| 2006/0089496 | A1 | 4/2006 | Lam et al. |
| 2006/0166960 | A1 | 7/2006 | Aslanian et al. |
| 2007/0004713 | A1 | 1/2007 | Barlaam et al. |
| 2007/0032475 | A1 | 2/2007 | Ye et al. |

FOREIGN PATENT DOCUMENTS

| GB | 1416872 | 12/1975 |
| JP | 08 225535 A1 | 9/1996 |
| WO | WO 94/22826 | 10/1994 |
| WO | WO 98/48800 | 11/1998 |
| WO | WO 01/42224 A1 | 6/2001 |
| WO | WO 01/74773 A2 | 10/2001 |
| WO | WO 03/004467 A2 | 1/2003 |
| WO | WO 03/082272 A1 | 10/2003 |
| WO | WO 2004/081011 A1 | 9/2004 |
| WO | WO 2005/115977 A1 | 12/2005 |
| WO | WO 2006/011042 A1 | 2/2006 |
| WO | WO 2006/019833 A1 | 2/2006 |
| WO | WO 2006/023462 A1 | 3/2006 |
| WO | WO 2006/040281 A1 | 4/2006 |
| WO | WO 2007/012613 A1 | 2/2007 |
| WO | WO 2007/107539 A1 | 9/2007 |
| WO | WO 2007/108936 A | 9/2007 |
| WO | WO 2007/115933 A1 | 10/2007 |
| WO | WO 2008/045371 A | 4/2008 |

OTHER PUBLICATIONS

Database Chemcats [Online] chemical abstract service. Ambinter Stock Screening Collection; Feb. 13, 2008.
Esbenshade et al., "Histamine H3 receptor antagonists: preclinical promise for treating obesity and cognitive disorders". Mol Interv. Apr. 2006;6(2):77-88.
Hancock et al., Perspectives on cognitive domains, H3 receptor ligands and neurological disease. Expert Opin Investig Drugs. Oct. 2004;13(10):1237-48.
Koh et al. "Conformational and structural features determining in vitro antimalarial activity in some indolo 3, 2-couinolines, anilinoquinolines and tetrahydroindolo3, 2-dbenzazepines". European Journal of Medicinal Chemistry. vol. 29, No. 2, 1994, p. 107-113.
Blandina, P. et al., "Inhibition of cortical acetylcholine release and cognitive performance by histamine H3 receptor activation in rats", Br J Pharmacol. Dec. 1996;119(8):1656-64.
Fox, G. B. et al., "Effects of histamine H(3) receptor ligands GT-2331 and ciproxifan in a repeated acquisition avoidance response in the spontaneously hypertensive rat pup", Behav Brain Res. Apr. 1, 2002;131(1-2):151-61.

(Continued)

Primary Examiner — Golam M Shameem
(74) Attorney, Agent, or Firm — Jennifer A. Kispert

(57) ABSTRACT

The present invention provides a compound of formula I and the use thereof for the treatment of a central nervous system disorder related to or affected by the histamine-3 receptor:

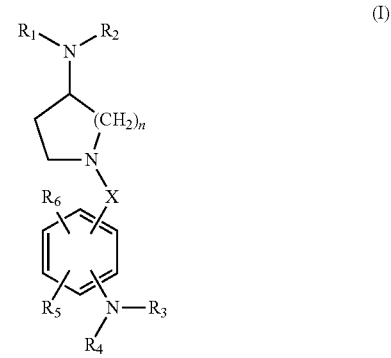

wherein the variables are described in the specification.

14 Claims, No Drawings

OTHER PUBLICATIONS

Komater, V.A., et al., "H3 receptor blockade by thioperamide enhances cognition in rats without inducing locomotor sensitization", Psychopharmacology (Berl). Jun. 2003;167(4):363-72.

Meguro, K. et al., "Effects of thioperamide, a histamine H3 antagonist, on the step-through passive avoidance response and histidine decarboxylase activity in senescence-accelerated mice", Pharmacol Biochem Behav. Mar. 1995;50(3):321-5.

Miyazaki, S. et al., "Effects of clobenpropit (VUF-9153), a histamine H3-receptor antagonist, on learning and memory, and on cholinergic and monoaminergic systems in mice", Life Sci. 1997;61(4):355-61.

PCT International Search Report, Written Opinion of the International Searching Authority for PCT/US2007/021474. International filing date Oct. 5, 2007.

Prast, H. et al., "Histaminergic neurons facilitate social memory in rats", Brain Res. Sep. 23, 1996;734(1-2):316-8.

N-SUBSTITUTED-AZACYCLYLAMINES AS HISTAMINE-3 ANTAGONISTS

CROSS REFERENCE TO RELATED APPLICATIONS

This application claims the benefit under 35 U.S.C. §119(e) to co-pending U.S. provisional application Ser. No. 60/850,143, filed Oct. 6, 2006, which is hereby incorporated by reference in its entirety.

FIELD OF THE INVENTION

The current invention relates to compounds that inhibit the H3 receptor and are useful as therapeutic agents in the treatment of a variety of central nervous system disorders related to or affected by the H3 receptor. This invention also provides therapeutic methods and pharmaceutical compositions useful for the treatment of central nervous system disorders related to or affected by the H3 receptor.

BACKGROUND OF THE INVENTION

The histamine-3 (H3) receptor is one of four histamine receptor subtypes (H1-H4), all of which are members of the larger G-protein-coupled receptor (GPCR) superfamily of receptors. The H3 receptor is predominantly expressed in the central nervous system. In the brain, it is located in regions associated with learning and memory such as the cerebral cortex, hippocampus and striatum. The H3 receptor acts as both auto- and hetero-receptor to regulate the release of histamine and other neurotransmitters. Within the cortex, the H3 receptor appears to directly modify GABA release from cortical interneurons. Antagonism of the H3 receptor produces a decrease in GABA release and disinhibition of the cortical cholinergic system, resulting in increased acetylcholine levels (Bacciottini, L. et al, Behavioral Brain Research, 124, 2001, 183-194). In addition to direct regulation of cholinergic neurotransmission, the H3 receptor has been shown to modulate the release of dopamine, serotonin and norepinephrine (Leurs, R., et al, Trends in Pharmacological Sciences, 19, 1998, 177-183). A postmortem study in humans suggests that a decrease in brain histamine levels may contribute to the cognitive decline which occurs in Alzheimer's disease, directly or through the cholinergic system (Panula, P., et al, Neuroscience, 82, 1998, 993-997). H3 agonists have been reported to impair memory in various tasks, such as object recognition, passive avoidance (Blandina, P., et al, British Journal of Pharmacology, 119(8), 1996, 1656-1664) and social olfactory memory (Prast, H., et al, 734, 1996, 316-318), whereas H3 antagonists have been reported to rescue impairments produced pharmacologically or genetically, i.e. Miyazaki, S., et al, Life Sciences, 61, 1997, 355-361; Meguro, K., et al, Pharmacology, Biochemistry and Behavior, 50, 1995, 321-325; Fox, G. B., et. al, Behavioral Brain Research, 131, 2002, 151-161; and Komater, V. A., et al, Psychopharmacology, 167, 2003, 363-372.

Accumulating neuroanatomical, neurochemical, pharmacological and behavioral data support the concept that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders.

Therefore, it is an object of this invention to provide compounds which are inhibitors of the H3 receptor and are useful as therapeutic agents in the treatment of a variety of central nervous system disorders related to or affected by the H3 receptor.

It is another object of this invention to provide therapeutic methods and pharmaceutical compositions useful for the treatment of central nervous system disorders related to or affected by the H3 receptor.

It is a feature of this invention that the compounds provided may also be useful to further study and elucidate the H3 receptor.

SUMMARY OF THE INVENTION

The present invention provides an N-substituted-azacyclylamine compound of formula I

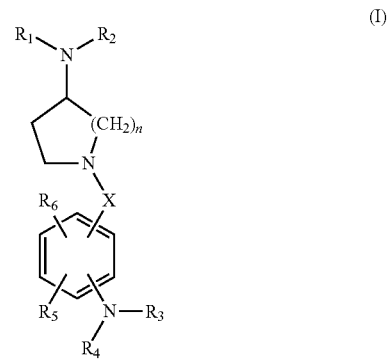

wherein
X is CO, $CH_2$ or $SO_m$;
n is an integer of 1, 2 or 3;
m is 0 or an integer of 1, or 2;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S;
$R_3$ and $R_4$ are taken together with the atom to which they are attached to form an optionally substituted fused polycyclic 9- to 15-membered ring system optionally containing one to three additional heteroatoms selected from N, O or S;
$R_5$ and $R_6$ are each independently H, halogen, $OR_8$ or an alkyl, alkenyl, alkynyl, cycloalkyl, cycloheteroalkyl, aryl or heteroaryl group each optionally substituted;
$R_8$ is H or an optionally substituted alkyl group; or a stereoisomer thereof or a pharmaceutically acceptable salt thereof.

The present invention also provides methods and compositions useful for the therapeutic treatment of central nervous system disorders related to or affected by the Histamine-3 receptor.

Another embodiment of the present invention provides use of a composition of any one of the embodiments described herein for the treatment of a central nervous system disorder related to or affected by the Histamine-3 receptor. More particularly, the present invention provides for use of a compound of any one of the embodiments described herein for the manufacture of a medicament for the treatment of a central nervous system disorder related to or affected by the Histamine-3 receptor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Alzheimer's disease (AD) is characterized by a progressive loss of memory and cognitive function and is the most common cause of dementia in the elderly. AD is believed to affect approximately 15-20 million people worldwide. The goal of treatment in AD, in addition to reversing the disease process, is to improve or at least slow the loss of memory and cognition and to maintain independent function in patients with mild to moderate disease. AD is characterized by numerous deficits in neurotransmitter function (Möller, H-J., European Neuropsychopharmacology, 9, 1999, S53-S59), further a postmortem study in humans suggests that a decrease in brain histamine levels may contribute to the cognitive decline associated with AD, directly or through the cholinergic system (Panula, P., et al, Neuroscience, 82, 1998, 993-997). Histamine-3 (H3) receptor antagonists have been reported to rescue impairments produced pharmacologically or genetically (Miyazaki, S., et al, Life Sciences, 61, 1997, 355-361; Meguro, K., et al, Pharmacology, Biochemistry and Behavior, 50, 1995, 321-325; Fox, G. B., et. al, Behavioral Brain Research, 131, 2002, 151-161; and Komater, V. A., et al, Psychopharmacology, 167, 2003, 363-372). Neuroanatomical, neurochemical, pharmacological and behavioral data support the belief that H3 receptor antagonists may improve cognitive performance in disease states such as mild cognitive impairment and Alzheimer's disease and may have therapeutic value in the treatment of attention deficit hyperactivity disorder (ADHD), schizophrenia, obesity and sleep disorders. To that end, compounds which inhibit the H3 receptor and act as H3 antagonists are earnestly sought.

Surprisingly it has now been found that N-substituted-azacyclylamine compounds of formula I demonstrate H3 affinity along with significant sub-type selectivity and function as H3 antagonists. Advantageously, said formula I compounds are effective therapeutic agents for the treatment of central nervous system (CNS) disorders associated with or affected by the H3 receptor. Accordingly, the present invention provides an N-substituted-pyrrolidin-3-ylamine compound of formula I

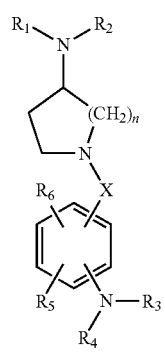

(I)

wherein
X is CO, $CH_2$ or $SO_m$;
n is an integer of 1, 2 or 3;
m is 0 or an integer of 1, or 2;
$R_1$ and $R_2$ are each independently H or an optionally substituted alkyl group or $R_1$ and $R_2$ may be taken together with the atom to which they are attached to form an optionally substituted 4- to 7-membered ring optionally containing one or two additional heteroatoms selected from N, O or S;
$R_3$ and $R_4$ are taken together with the atom to which they are attached to form an optionally substituted fused polycyclic 9- to 15-membered ring system optionally containing one to three additional heteroatoms selected from N, O or S;
$R_5$ and $R_6$ are each independently H, halogen, $OR_8$ or an alkyl, alkenyl, alkynyl, cycloalkyl, cycloheteroalkyl, aryl or heteroaryl group each optionally substituted;
$R_8$ is H or an optionally substituted alkyl group; or a stereoisomer thereof or a pharmaceutically acceptable salt thereof.

In another embodiment, X is CO or $CH_2$. More particularly, n is 1. In another embodiment, $R_5$ and $R_6$ are each independently H or halogen. In another embodiment, $R_1$ and $R_2$ are taken together with the atom to which they are attached to form an optionally substituted 5-, 6- or 7-membered ring. In another embodiment, $R_3$ and $R_4$ are taken together with the atom to which they are attached to form a fused bicyclic 9- to 11-membered ring system. In another embodiment, $R_3$ and $R_4$ are taken together with the atom to which they are attached to form an optionally substituted indole, indazole, benzimidazole or carbazole ring. In another embodiment, X is CO and $R_1$ and $R_2$ are taken together with the atom to which they are attached to form an optionally substituted 5-membered ring. More particularly, $R_3$ and $R_4$ are taken together with the atom to which they are attached to form an optionally substituted indole, indazole or benzimidazole ring.

Another embodiment provides a method for the treatment of a central nervous system disorder related to or affected by the Histamine-3 receptor in a patient in need thereof which comprises providing to said patient a therapeutically effective amount of a compound as described herein. In a more particular embodiment, said disorder is a cognitive disorder, a developmental disorder or a sleep disorder. In another embodiment, said disorder is selected from the group consisting of: Alzheimer's disease; a learning disorder; attention deficit disorder; and schizophrenia.

Additional embodiments of the present invention include a method for the inhibition of the H3 receptor which comprises contacting said receptor with an effective amount of a compound as described herein.

Furthermore, a pharmaceutical composition which comprises a pharmaceutically acceptable carrier and an effective amount of a compound as described herein is provided.

A further aspect of the invention provides process for the preparation of a compound of formula I

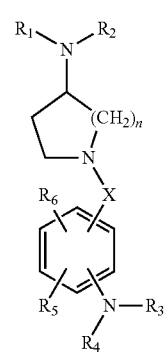

(I)

wherein

X is CO, CH$_2$ or SO$_m$;

n is an integer of 1, 2 or 3;

m is 0 or an integer of 1 or 2;

R$_1$ and R$_2$ are each independently H or an optionally substituted alkyl group or R$_1$ and R$_2$ may be taken together with the atom to which they are attached to form an optionally substituted 4- to 7-membered ring optionally containing one or two additional heteroatoms selected from N, O or S R$_3$ and R$_4$ are taken together with the atom to which they are attached to form an optionally substituted fused polycyclic 9- to 15-membered ring system optionally containing one to three additional heteroatoms selected from N, O or S;

R$_5$ and R$_6$ are each independently H, halogen, OR8 or an alkyl, alkenyl, alkynyl, cycloalkyl, cycloheteroalkyl, aryl or heteroaryl group each optionally substituted;

R$_8$ is H or an optionally substituted alkyl group; which process comprises reacting a compound of formula II

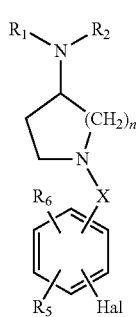
(II)

wherein

X, n, R$_1$, R$_2$, R$_5$ and R$_6$ are as described for formula I and Hal represents F, Cl, Br or I with a cyclic amine of formula III

(III)

wherein

R$_3$ and R$_4$ are as described for formula I in the presence of a base.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents, e.g., 1 to 5 or 1 to 3 substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl (e.g., heteroaryl or cycloheteroalkyl) or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term alkyl includes both straight chain and branched-chain (unless defined otherwise) monovalent saturated hydrocarbon moiety of 1-12 carbon atoms, preferably 1-6 carbon atoms, more preferably 'lower' alkyl of 1-4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Alkyl groups can be optionally substituted. Suitable alkyl substitutions include, but are not limited to, CN, OH, NR$_1$R$_2$, halogen, phenyl, carbamoyl, carbonyl, alkoxy or aryloxy.

As used herein, the term haloalkyl designates a C$_n$H$_{2n+}$ group having from one to 2n+1 halogen atoms which may be the same or different. Examples of haloalkyl groups include CF$_3$, CH$_2$C$_1$, C$_2$H$_3$BrCl, C$_3$H$_5$F$_2$, or the like.

The term halogen, as used herein, designates fluorine, chlorine, bromine, and iodine.

The term alkenyl, as used herein, refers to either a straight chain or branched-chain monovalent hydrocarbon moiety containing at least one double bond and having from 2-12 carbon atoms, preferably 2-6 carbon atoms, more preferably 2-4 carbon atoms. Such hydrocarbon alkenyl moieties may exist in the E or Z configurations. The compounds of this invention are meant to include all possible E and Z configurations. Examples of hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term alkynyl, as used in the specification and claims, designates either a straight chain or branched chain monovalent hydrocarbon moiety containing at least one triple bond and having from 2-12 carbon atoms, preferably 2-6 carbon atoms, more preferably 2-4 carbon atoms. Examples of hydrocarbon alkynyl moieties include, but are not limited to, propynyl, butynyl, 1,3-butadiynyl, pentynyl, hexynyl, or the like.

The term cycloalkyl, as used herein, refers to a monocyclic, bicyclic, tricyclic, fused, bridged, or spiro monovalent saturated hydrocarbon moiety of 3-10 carbon atoms. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, or the like.

The term cycloheteroalkyl, as used herein, designates a 5-7 membered ring system containing 1, 2 or 3 heteroatoms, which may be the same or different, selected from N, O or S and optionally containing one double bond. Exemplary of the cycloheteroalkyl ring systems included in the term as designated herein are the following rings wherein X$_1$ is NR', O or S and R' is H or an optional substituent as defined hereinabove.

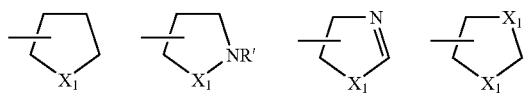

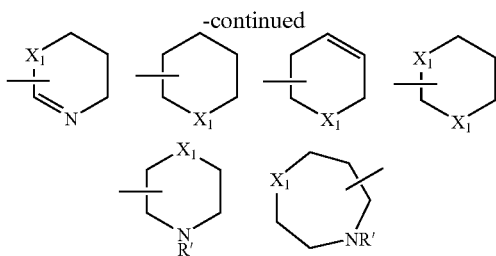

The term aryl, as used herein, refers to an aromatic carbocyclic moiety of up to 20 carbon atoms, e.g. 6-14 carbon atoms which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, biphenyl, anthryl, phenanthryl, fluorenyl, indanyl, acenaphthenyl, or the like.

The term heteroaryl as used herein designates an aromatic heterocyclic ring system, e.g., of 5-20 ring atoms, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atoms are optionally oxidized, or the nitrogen atom is optionally quaternized. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, quinoline, isoquinoline, quinazoline, quinoxaline, purine, or the like.

Exemplary of the fused polycyclic 9- to 15-membered ring system formed when $R_3$ and $R_4$ are taken together with the nitrogen atom to which they are attached are indolyl, indazolyl, benzimidazolyl, tetrahydrocarbazolyl, carbazolyl, hexahydroindolizinoindolonyl, tetrahydropyranoindolyl, azaindolyl, imidazopyridinyl, indolinyl, tetrahydroquinolinlyl, pyridoindolyl, dihydrodibenzoazepinyl, or the like. Preferably, the polycyclic ring systems comprise two or three fused rings. In a preferred embodiment, the fused polycyclic ring systems are bicyclic 9- to 11-membered ring systems.

Unless otherwise stated, structures depicted herein are also meant to include all stereochemical forms of the structure; i.e., the (R)- and (S)-absolute stereochemical configuration for each asymmetric center. Therefore, single stereoisomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen atom by a deuterium or tritium, or the replacement of a carbon atom with $^{13}C$- or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine where 'lower' denotes 1-6, e.g., 1-4 carbon atoms, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts that are unsuitable for pharmaceutical uses but which can be employed, for example, in the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Preferred compounds of the invention are those compounds of formula I wherein X is CO or $CH_2$. Another group of preferred compounds is those formula I compounds wherein n is 1. Also preferred are those formula I compounds wherein $R_5$ and $R_6$ are each independently H or halogen.

More preferred compounds of the invention are those compounds of formula I wherein X is CO or $CH_2$ and $R_1$ and $R_2$ are taken together with the atom to which they are attached to form an optionally substituted 5-membered ring. Another group of more preferred compounds is those compounds of formula I wherein X is CO or $CH_2$ and $R_3$ and $R_4$ are taken together with the atom to which they are attached to form an optionally substituted indole, indazole, benzimidazole or carbazole ring. A further group of more preferred compounds are those compounds of formula I wherein X is CO; n is 1; $R_1$ and $R_2$ are taken together with the atom to which they are attached to form an optionally substituted 5-membered ring; and $R_3$ and $R_4$ are taken together with the atom to which they are attached to form an optionally substituted indole, indazole, benzimidazole or carbazole ring.

The group $NR^3R^4$ may be para to the —X— group in the phenyl ring to which they are attached.

In one embodiment, the compound is selected from the following:

N,N-Dimethyl-1-[4-(2-phenyl-1H-benzimidazol-1-yl)benzoyl]pyrrolidin-3-ylamine;
(3-S)-N,N-Dimethyl-1-[4-(2-phenyl-1H-benzimidazol-1-yl)benzoyl]pyrrolidin-3-ylamine;
(3-R)-N,N-Dimethyl-1-[4-(2-phenyl-1H-benzimidazol-1-yl)benzoyl]pyrrolidin-3-ylamine;
N,N-Dimethyl-1-[4-(6-fluoro-1H-benzimidazol-1-yl)benzoyl]pyrrolidin-3-ylamine;
N,N-Dimethyl-1-[4-(6-methyl-1H-benzimidazol-1-yl)benzoyl]pyrrolidin-3-ylamine;

N,N-Dimethyl-1-[4-(5-fluoro-1H-benzimidazol-1-yl)benzoyl]pyrrolidin-3-ylamine;
N,N-Dimethyl-1-[4-(4-fluoro-1H-benzimidazol-1-yl)benzoyl]pyrrolidin-3-ylamine;
N,N-Dimethyl-1-[3-(1H-benzimidazol-1-yl)benzoyl]pyrrolidin-3-ylamine;
N,N-Dimethyl1-[4-(1H-indol-1-yl)benzoyl]pyrrolidin-3-ylamine;
N,N-Dimethyl1-[4-(2,3,4,9-tetrahydro-1H-carbazole)benzoyl]pyrrolidin-3-ylamine;
N,N-Dimethyl1-[4-(2-methyl-1H-indol-1-yl)benzoyl]pyrrolidin-3-ylamine;
N,N-Dimethyl1-[4-(2-phenyl-1H-indol-1-yl)benzoyl]pyrrolidin-3-ylamine;
N,N-Dimethyl1-[4-(5-methoxy-1H-indol-1-yl)benzoyl]pyrrolidin-3-ylamine;
N,N-Dimethyl1-[4-(5-methoxy-2-phenyl-1H-indol-1-yl)benzoyl]pyrrolidin-3-ylamine;
N,N-Dimethyl1-[4-(7-aza-1H-indol-1-yl)benzoyl]pyrrolidin-3-ylamine;
N,N-Dimethyl1-[4-(1H-benzo[d]imidazol-1-yl)benzoyl]pyrrolidin-3-ylamine;
N,N-Dimethyl1-[4-(2-methyl-1H-benzo[d]imidazol-1-yl)benzoyl]pyrrolidin-3-ylamine;
N,N-Dimethyl1-[4-(5-hydroxy-1H-indol-1-yl)benzoyl]pyrrolidin-3-ylamine;
N,N-Dimethyl1-[4-(1,2,3,4-tetrahydroquinolin-1-yl)benzoyl]pyrrolidin-3-ylamine;
N,N-Dimethyl1-[4-(5-fluoro-1H-indol-1-yl)benzoyl]pyrrolidin-3-ylamine;
N,N-Dimethyl1-[4-(3-cyano-1H-indol-1-yl)benzoyl]pyrrolidin-3-ylamine;
N,N-Dimethyl1-[4-(2-phenyl-1H-imidazol-1-yl)benzoyl]pyrrolidin-3-ylamine;
1'-[4-(2-Phenyl-1H-benzimidazol-1-yl)benzoyl]-1,3'-bipyrrolidine;
1'-[4-(5-Chloro-2-methyl-1H-benzimidazol-1-yl)benzoyl]-1,3'-bipyrrolidine;
1'-[4-(6-Chloro-2-methyl-1H-benzimidazol-1-yl)methyl]benzoyl]-1,3'-bipyrrolidine;
1'-[4-(6-Methyl-1H-benzimidazol-1-yl)benzoyl]-1,3'-bipyrrolidine;
1'-[4-(5-Fluoro-1H-benzimidazol-1-yl)benzoyl]-1,3'-bipyrrolidine;
(2-R)-1'-[4-(1H-Benzimidazol-1-yl)benzoyl]-2-methyl-1,3'-bipyrrolidine;
(3'-R)-1'-[4-[(2-Methyl-1H-benzimidazol-1-yl)benzoyl]-1,3'-bipyrrolidine;
(3'-S)-[4-(1H-Indol-1-yl)benzoyl]-1,3'-bipyrrolidine;
(3'-S)-[4-(1H-Indazol-1-yl)benzoyl]-1,3'-bipyrrolidine;
(3'-S)-1'-[4-[(5-Chloro-2-methyl-1H-benzimidazol-1-yl)benzoyl]-1,3'-bipyrrolidine;
(3'-S)-1'-[4-[(6-Chloro-2-methyl-1H-benzimidazol-1-yl)benzoyl]-1,3'-bipyrrolidine;
(3'-S)-1'-[4-[(7-Chloro-1H-indol-1-yl)benzoyl]-1,3'-bipyrrolidine;
9-{4-[(3'S)-1,3'-Bipyrrolidin-1-ylcarbonyl]phenyl}-9H-carbazole;
(3'-S)-1'-[4-(1S)-1-(2-Methyl-1H-benzimidazol-1-yl)benzoyl]-1,3'-bipyrrolidine;
(3'-S)-1'-[4-(1R)-1-(2-Methyl-1H-benzimidazol-1-yl)benzoyl]-1,3'-bipyrrolidine;
(3'-S)-1'-[4-(1H-Benzimidazol-1-yl)benzyl]-2-methyl-1,3'-bipyrrolidine;
N,N-Dimethyl-1-[4-(2-phenyl-1H-benzimidazol-1-yl)benzyl]pyrrolidin-3-ylamine;
(3-S)-N,N-Dimethyl-1-[4-(2-phenyl-1H-benzimidazol-1-yl)benzyl]pyrrolidin-3-ylamine;
(3-R)-N,N-Dimethyl-1-[4-(2-phenyl-1H-benzimidazol-1-yl)benzyl]pyrrolidin-3-ylamine;
N,N-Dimethyl-1-[4-(6-fluoro-1H-benzimidazol-1-yl)benzyl]pyrrolidin-3-ylamine;
N,N-Dimethyl-1-[4-(6-methyl-1H-benzimidazol-1-yl)benzyl]pyrrolidin-3-ylamine;
N,N-Dimethyl-1-[4-(5-fluoro-1H-benzimidazol-1-yl)benzyl]pyrrolidin-3-ylamine;
N,N-Dimethyl-1-[4-[(4-fluoro-1H-benzimidazol-1-yl)benzyl]pyrrolidin-3-ylamine;
N,N-Dimethyl-1-[3-(1H-benzimidazol-1-yl)benzyl]pyrrolidin-3-ylamine;
N,N-Dimethyl1-[4-(1H-indol-1-yl)benzyl]pyrrolidin-3-ylamine;
N,N-Dimethyl1-[4-(2,3,4,9-tetrahydro-1H-carbazole)benzyl]pyrrolidin-3-ylamine;
a stereoisomer thereof; or a pharmaceutically acceptable salt thereof.

Exemplary compounds of the invention are shown in the following compound table:

COMPOUND TABLE

| Compound | IUPAC name |
|---|---|
| 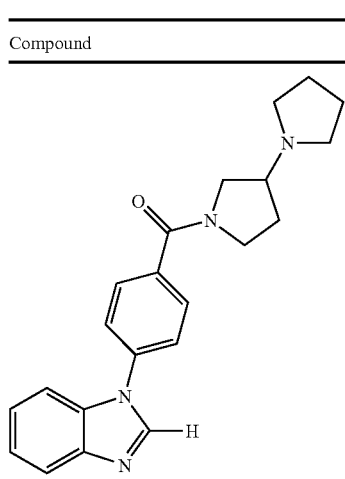 | 1'-[4-(1H-benzimidazol-1-yl)benzoyl]-1,3'-bipyrrolidine |

-continued
| Compound | IUPAC name |
|---|---|
|  ABS | (3'S)-1'-[4-(1H-benzimidazol-1-yl)benzoyl]-1,3'-bipyrrolidine |
| 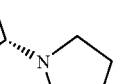 ABS | (2R,3'S)-1'-[4-(1H-benzimidazol-1-yl)benzoyl]-2-methyl-1,3'-bipyrrolidine |
| 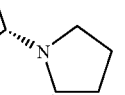 ABS | (2S,3'S)-1'-[4-(1H-benzimidazol-1-yl)benzoyl]-2-methyl-1,3'-bipyrrolidine |
| 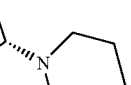 ABS | 1-(4-{[(3S)-3-(3-methylpiperidin-1-yl)pyrrolidin-1-yl]carbonyl}phenyl)-1H-benzimidazole |

-continued

| Compound | IUPAC name |
|---|---|
| ABS | 1-(4-{[(3S)-3-(4-methylpiperidin-1-yl)pyrrolidin-1-yl]carbonyl}phenyl)-1H-benzimidazole |
| ABS | 1-(4-{[(3S)-3-(4-methylpiperazin-1-yl)pyrrolidin-1-yl]carbonyl}phenyl)-1H-benzimidazole |
| ABS | 1-(4-{[(3S)-3-azepan-1-ylpyrrolidin-1-yl]carbonyl}phenyl)-1H-benzimidazole |
| ABS | 1-(4-{[(3S)-3-(2-methylpiperidin-1-yl)pyrrolidin-1-yl]carbonyl}phenyl)-1H-benzimidazole |

-continued
| Compound | IUPAC name |
|---|---|
| 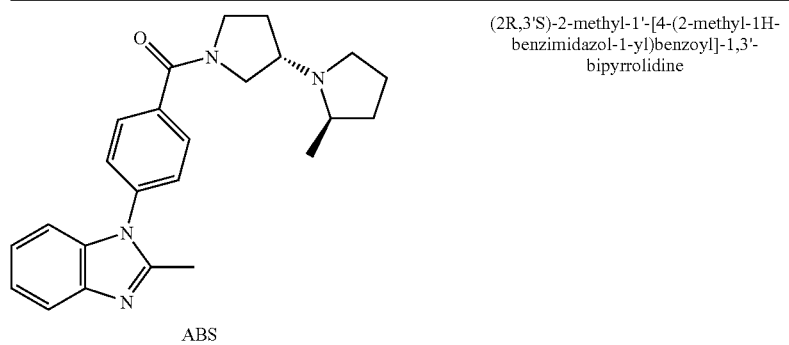 ABS | (2R,3'S)-2-methyl-1'-[4-(2-methyl-1H-benzimidazol-1-yl)benzoyl]-1,3'-bipyrrolidine |
| 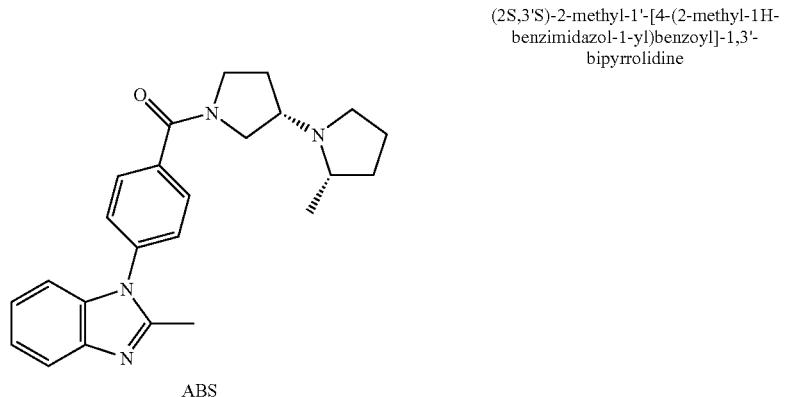 ABS | (2S,3'S)-2-methyl-1'-[4-(2-methyl-1H-benzimidazol-1-yl)benzoyl]-1,3'-bipyrrolidine |
| 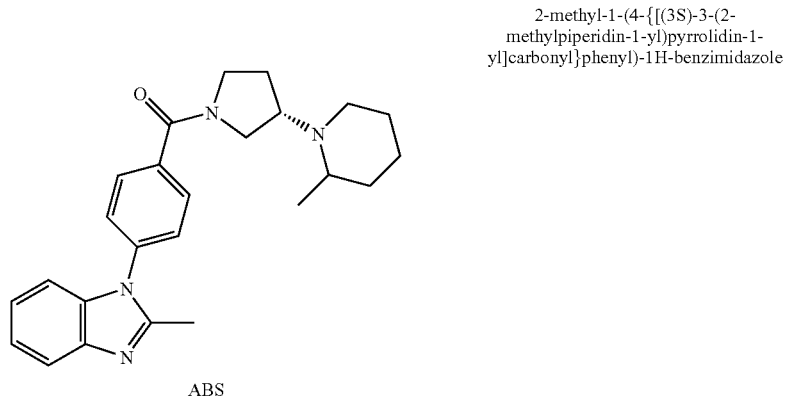 ABS | 2-methyl-1-(4-{[(3S)-3-(2-methylpiperidin-1-yl)pyrrolidin-1-yl]carbonyl}phenyl)-1H-benzimidazole |
| 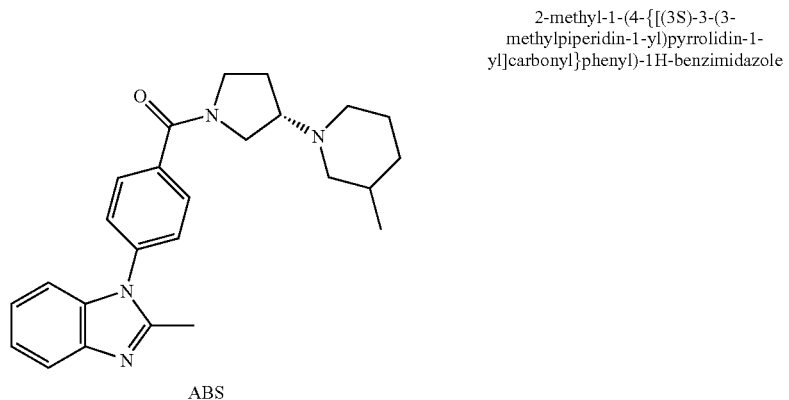 ABS | 2-methyl-1-(4-{[(3S)-3-(3-methylpiperidin-1-yl)pyrrolidin-1-yl]carbonyl}phenyl)-1H-benzimidazole |

| Compound | IUPAC name |
|---|---|
| ABS | 2-methyl-1-(4-{[(3S)-3-(4-methylpiperidin-1-yl)pyrrolidin-1-yl]carbonyl}phenyl)-1H-benzimidazole |
| ABS | 2-methyl-1-(4-{[(3S)-3-(4-methylpiperazin-1-yl)pyrrolidin-1-yl]carbonyl}phenyl)-1H-benzimidazole |
| ABS | (3'S)-1'-[4-(2-methyl-1H-benzimidazol-1-yl)benzoyl]-1,3'-bipyrrolidine |
| ABS | 2-methyl-1-(4-{[(3S)-3-piperidin-1-ylpyrrolidin-1-yl]carbonyl}phenyl)-1H-benzimidazole |

| Compound | IUPAC name |
|---|---|
| 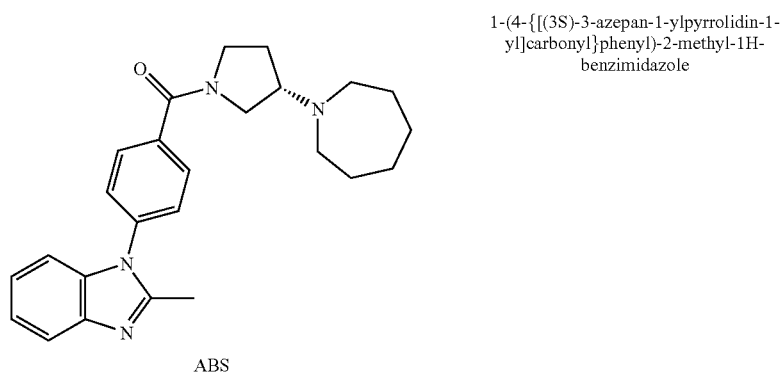 ABS | 1-(4-{[(3S)-3-azepan-1-ylpyrrolidin-1-yl]carbonyl}phenyl)-2-methyl-1H-benzimidazole |
| | 1-(4-{[(3S)-3-piperidin-1-ylpyrrolidin-1-yl]carbonyl}phenyl)-1H-benzimidazole |
| 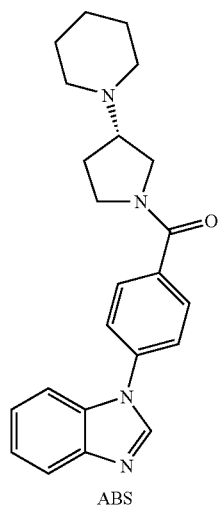 ABS | |
| | (3'S)-1'-[4-(1H-benzimidazol-1-yl)benzyl]-1,3'-bipyrrolidine |
| 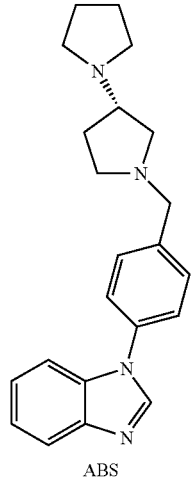 ABS | |

-continued
| Compound | IUPAC name |
|---|---|
| 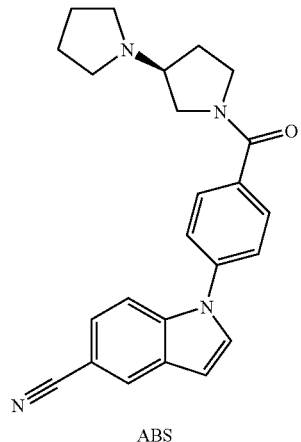 ABS | 1-{4-[(3'S)-1,3'-bipyrrolidin-1'-ylcarbonyl]phenyl}-1H-indole-5-carbonitrile |
| 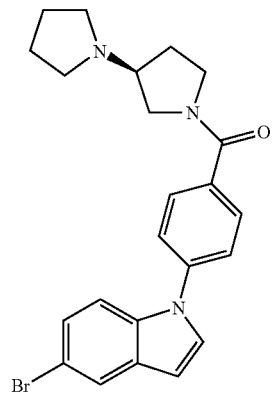 ABS | (3'S)-1'-[4-(5-bromo-1H-indol-1-yl)benzoyl]-1,3'-bipyrrolidine |
| 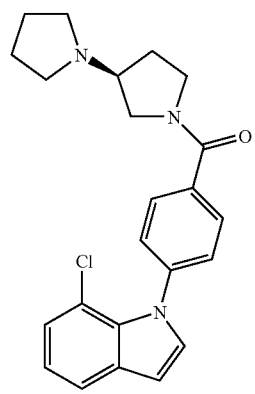 ABS | (3'S)-1'-[4-(7-chloro-1H-indol-1-yl)benzoyl]-1,3'-bipyrrolidine |

-continued
| Compound | IUPAC name |
|---|---|
| 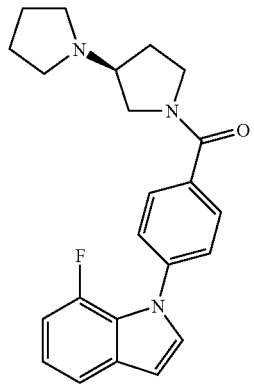 | (3'S)-1'-[4-(7-fluoro-1H-indol-1-yl)benzoyl]-1,3'-bipyrrolidine |
| 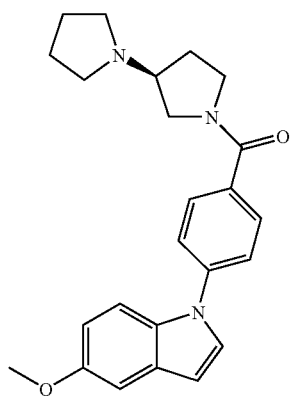 | (3'S)-1'-[4-(5-methoxy-1H-indol-1-yl)benzoyl]-1,3'-bipyrrolidine |
| 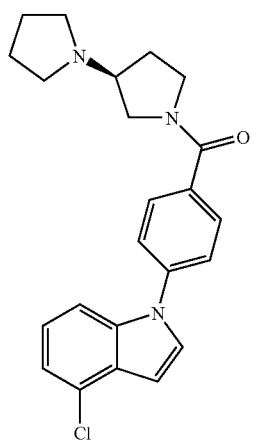 | (3'S)-1'-[4-(4-chloro-1H-indol-1-yl)benzoyl]-1,3'-bipyrrolidine |

-continued
| Compound | IUPAC name |
|---|---|
| 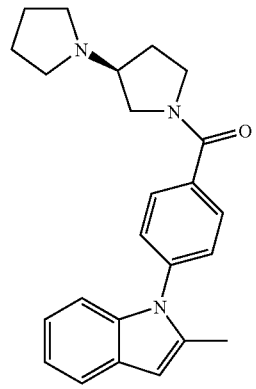 ABS | (3'S)-1'-[4-(2-methyl-1H-indol-1-yl)benzoyl]-1,3'-bipyrrolidine |
| 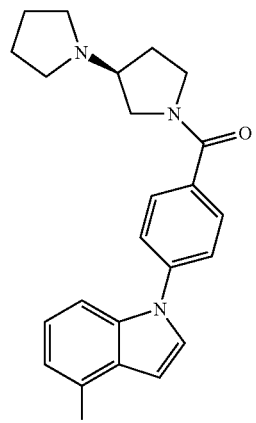 ABS | (3'S)-1'-[4-(4-fluoro-1H-indol-1-yl)benzoyl]-1,3'-bipyrrolidine |
| 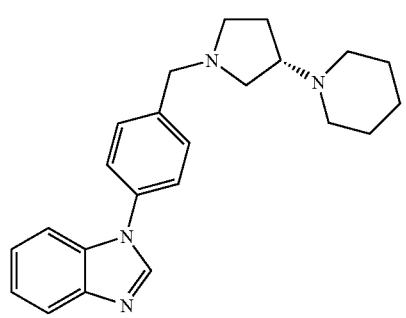 ABS | 1-(4-{[(3S)-3-piperidin-1-ylpyrrolidin-1-yl]methyl}phenyl)-1H-benzimidazole |

| Compound | IUPAC name |
|---|---|
| 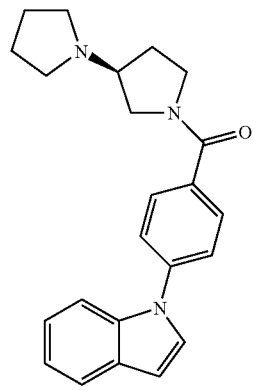 ABS | (3'S)-1'-[4-(1H-indol-1-yl)benzoyl]-1,3'-bipyrrolidine |
| 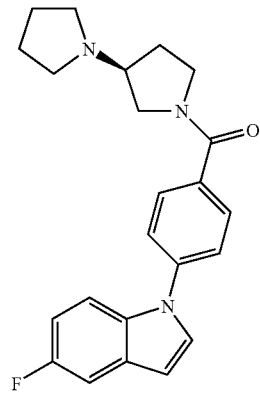 ABS | (3'S)-1'-[4-(5-fluoro-1H-indol-1-yl)benzoyl]-1,3'-bipyrrolidine |
| 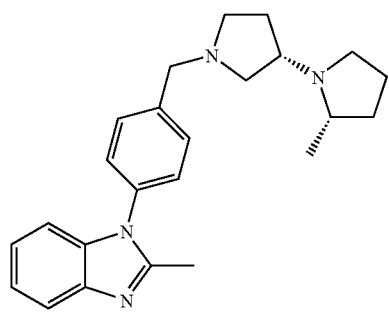 ABS | (2S,3'S)-2-methyl-1'-[4-(2-methyl-1H-benzimidazol-1-yl)benzyl]-1,3'-bipyrrolidine |

-continued

| Compound | IUPAC name |
|---|---|
| ABS | (3'S)-1'-[4-(5-fluoro-2H-indazol-2-yl)benzoyl]-1,3'-bipyrrolidine |
| ABS | (3'S)-1'-[4-(5-fluoro-1H-indazol-1-yl)benzoyl]-1,3'-bipyrrolidine |
| ABS | 1-{4-[(3'S)-1,3'-bipyrrolidin-1'-ylcarbonyl]phenyl}-1H-indazole-5-carbonitrile |

-continued
| Compound | IUPAC name |
|---|---|
| 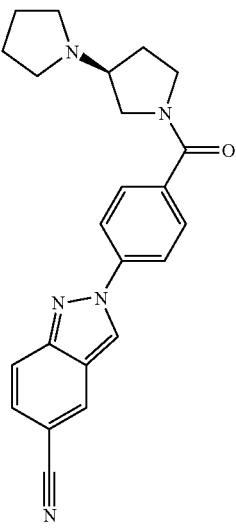 ABS | 2-{4-[(3'S)-1,3'-bipyrrolidin-1'-ylcarbonyl]phenyl}-2H-indazole-5-carbonitrile |
| 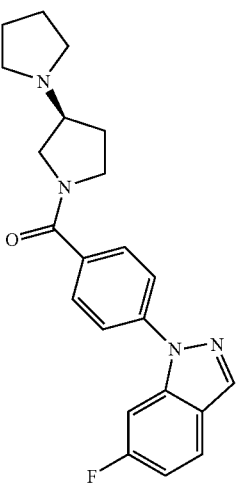 ABS | (3'S)-1'-[4-(6-fluoro-1H-indazol-1-yl)benzoyl]-1,3'-bipyrrolidine |
| 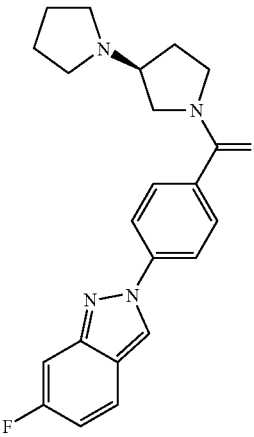 ABS | (3'S)-1'-[4-(6-fluoro-2H-indazol-2-yl)benzoyl]-1,3'-bipyrrolidine |

| Compound | IUPAC name |
|---|---|
| 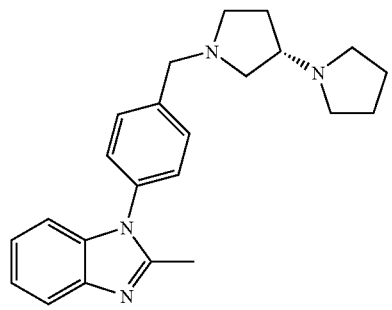<br>ABS | (3'S)-1'-[4-(2-methyl-1H-benzimidazol-1-yl)benzyl]-1,3'-bipyrrolidine |
| 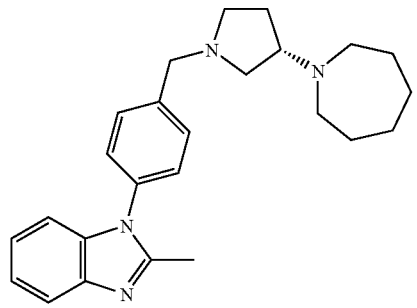<br>ABS | 1-(4-{[(3S)-3-azepan-1-ylpyrrolidin-1-yl]methyl}phenyl)-2-methyl-1H-benzimidazole |
| 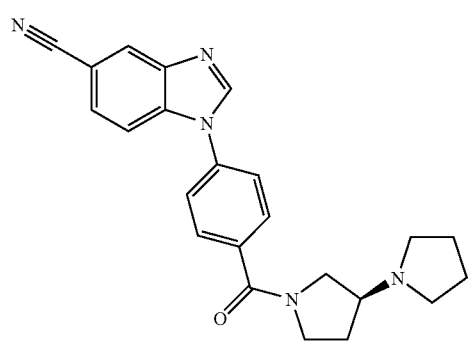<br>ABS | 1-{4-[(3'S)-1,3'-bipyrrolidin-1'-ylcarbonyl]phenyl}-1H-benzimidazole-5-carbonitrile |
| 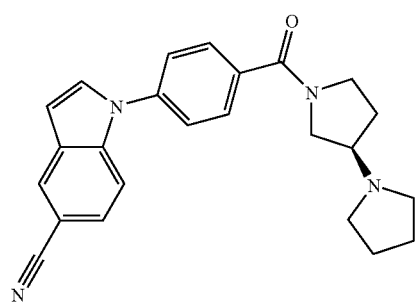<br>RAC | 1-{4-[(3'R)-1,3'-bipyrrolidin-1'-ylcarbonyl]phenyl}-1H-indole-5-carbonitrile |

Advantageously, the present invention provides a method for the preparation of a compound of formula I which comprises reacting a compound of formula II with a cyclic amine of formula III in the presence of a base optionally in the presence of a solvent. The process is shown in Scheme I wherein Hal represents F, Cl, Br or I.

SCHEME I

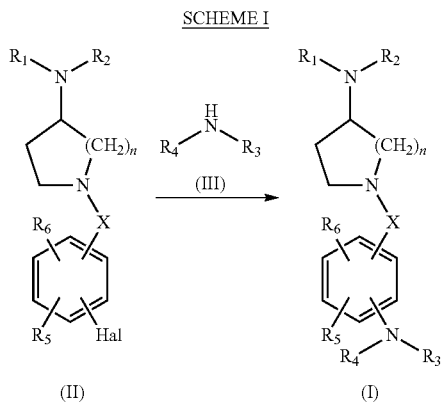

(II)  (I)

Bases suitable for use in the method of invention include $Cs_2CO_3$, $K_2CO_3$, $Na_2CO_3$, NaH, or any conventional base capable of removing a proton from a basic cyclic amine nitrogen atom.

Solvents suitable for use in the method of the invention include tetrahydrofuran, dimethyl formamide, dimethylsulfoxide, acetonitrile, or the like.

Compounds formula II may be prepared using conventional synthetic methods and, if required, standard isolation or separation techniques. For example compounds of formula II wherein X is CO (IIa) may be prepared by reacting a halobenzoic acid of formula IV with an aminopyrrolidine, -piperidine or -azepine of formula V in the presence of an amide coupling reagent such as benzotriazol-1-yl-oxytripyrrolidinophosphonium hexafluorophosphate (PyBOP) to give the desired compound of formula IIa. The reaction is shown in Scheme II wherein Hal is F, Cl, Br or I.

SCHEME II

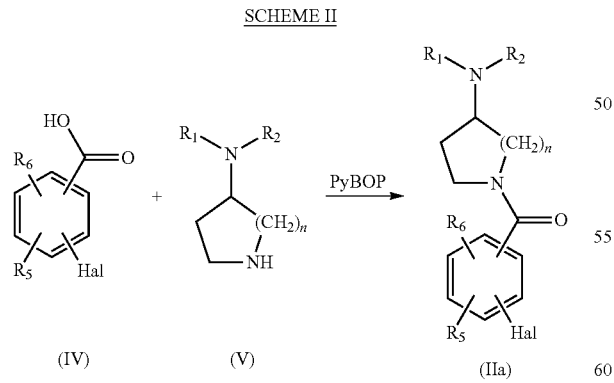

(IV)  (V)  (IIa)

Compounds of formula I wherein X is $CH_2$ (Ib) may be readily prepared by reducing the compounds of formula Ia wherein X is CO (Ia) with a suitable reducing agent such as $BH_3$ or $LiAlH_4$ give the desired compounds. The reaction is shown in Scheme III.

SCHEME III

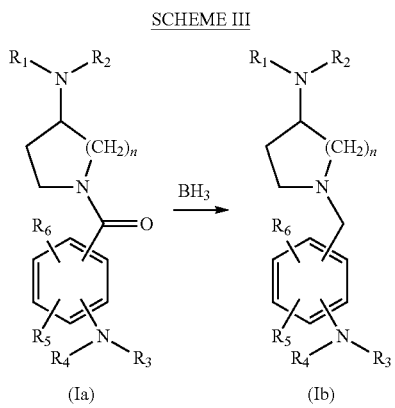

(Ia)  (Ib)

Alternatively, compounds of formula I wherein X is CO (Ia) may be prepared by reacting a 4-halobenzoate of formula VI with a cyclic amine of formula III via a transition metal-catalyze amination reaction or conversely, through nucleophilic aromatic substitution, to afford the benzoic acid of formula VII; followed by reacting the formula VII benzoic acid with an appropriate amine of formula V to give the desired compound of formula Ia. The reaction is shown in Scheme IV wherein R is lower alkyl.

SCHEME IV

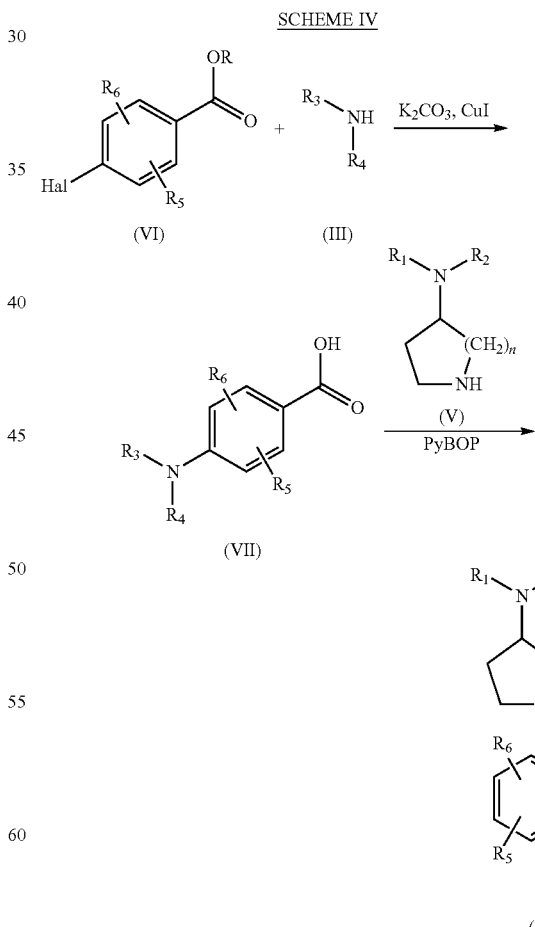

(Ia)

Compounds of formula I wherein X is $SO_2$ (Ic) may be prepared in a manner similar to that described in Schemes IV by replacing the benzoic acid of formula VII with the corresponding phenyl sulfonyl chloride. For example the phenylsulfonyl chloride of formula VII may be reacted with aminoazine of formula V to give the desired compound of formula Ic. The reaction is shown in Scheme V.

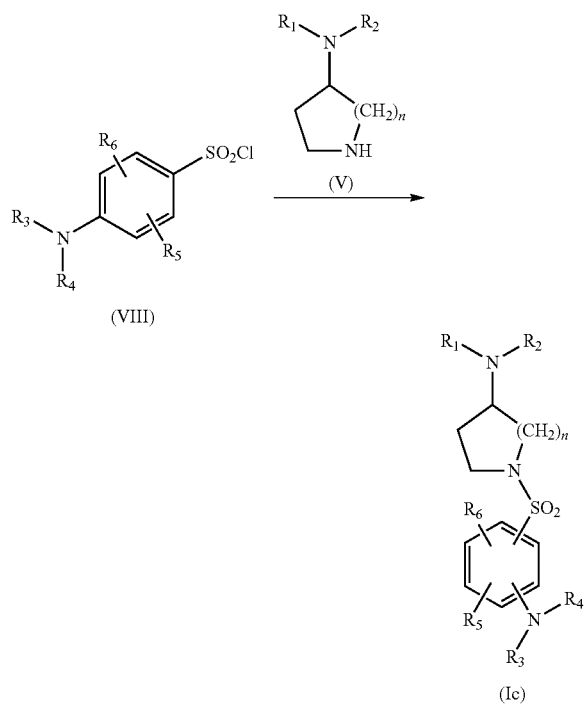

Compounds of formula I wherein X is S or SO may be prepared by reducing the compound of formula Ic with a suitable reducing agent to give the corresponding sulfinyl or thio compounds of formula I.

Advantageously, the formula I compounds of the invention are useful for the treatment of CNS disorders related to or affected by the Histamine-3 receptor including cognitive disorders, for example Alzheimer's disease, mild cognitive impairment, attention deficit hyperactivity disorder, schizophrenia, memory loss, sleep disorders, obesity or the like. Accordingly, the present invention provides a method for the treatment of a disorder of the central nervous system related to or affected by the Histamine-3 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition or learning or a cognitive disorder such as Alzheimer's disease or attention deficit hyperactivity disorder; a method for the treatment of a mild cognitive disorder, a method for the treatment of a developmental disorder such as schizophrenia and/or as an antipsychotic; a method for the treatment of a sleep disorder such as narcolepsy; or any other CNS disease or disorder associated with or related to the H3 receptor. Additionally, the compounds can be used to reduce methamphetamine (MAMPH) hyperactivity, enhances prepulse (PPI) inhibition, improve or increase: memory consolidation, spatial orientation, social recognition, working memory, attention and impulsivity, sensory gating and/or psychosis, or inhibitory avoidance.

In one embodiment, the present invention provides a method for treating attention deficit hyperactivity disorders (ADHD, also known as Attention Deficit Disorder or ADD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administration of the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered by intranasal or intrabronchial inhalation or insufflation, for example the compounds of formula I may be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, or the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The terms HPLC and $^1$H NMR designate high performance liquid chromatography and proton nuclear magnetic resonance, respectively. The term MS designates mass spectroscopy with (+) referring to the positive mode which generally gives a M+1 (or M+H) absorption where M=the molecular mass. Spectroscopic analysis for all compounds is obtained by MS, $^1$H NMR, or both.

The terms DMF, THF and Et$_2$O designate dimethyl formamide, tetrahydrofuran and diethyl ether, respectively. Unless otherwise noted, all parts are parts by weight.

EXAMPLES

Example 1

Method A

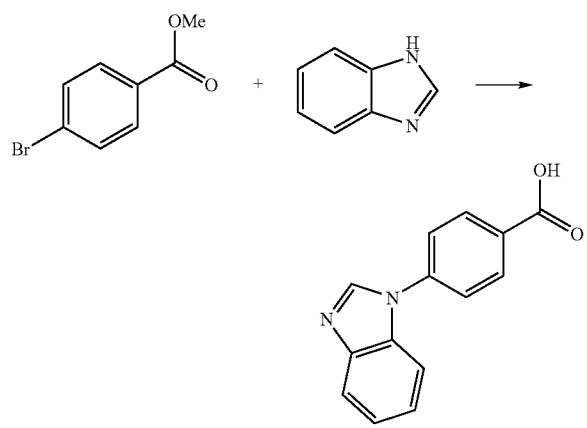

A mixture of benzimidazole (0.12 g, 1 mmol), methyl 4-bromobenzoate (0.11 g, 0.5 mmol), potassium carbonate (0.14 g, 1 mmol) and a catalytic amount of copper iodide (9.5 mg, 0.05 mmol) in 1 ml of N-methylpyrrolidinone is heated in a CEM microwave at 200° C. The reaction is monitored for completion by HPLC/MS. After 2 h at 200° C., the reaction mixture is concentrated under vacuum. The resultant residue is partitioned between ethyl acetate and water. The basic aqueous layer is separated, acidified to neutral pH and filtered. The filtercake is dried to obtain the title acid, identified by NMR and mass spectral analyses.

Method B

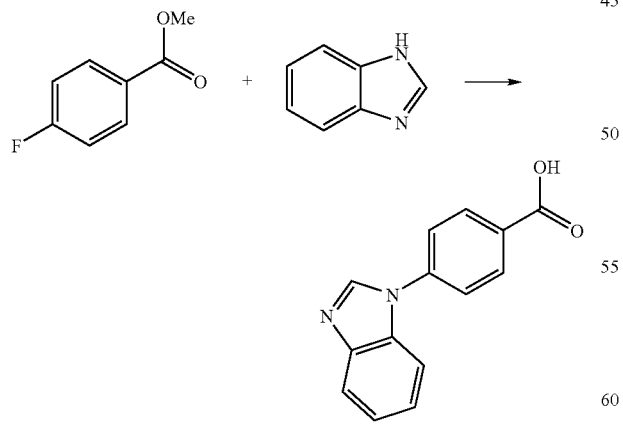

To a solution of (2.3 g, 19.46 mmol) 1H-benzimidazole in DMF (80 mL) at 0° C. was added sodium hydride (0.78 g, 19.46 mol, 60 wt. %) and the reaction mixture was stirred at 0° C. for 30 minutes, then at room temperature for 1 hour. Methyl 4-fluorobenzoate (3.0 g, 19.46 mmol) was then added and the reaction mixture was heated at 85° C. for 24 h. The reaction mixture was cooled to room temperature, diluted with water (300 mL) and extracted with dichloromethane (4×250 mL). The combined organic layers were washed with water (2×250 mL), saturated aqueous sodium chloride (200 mL), dried (magnesium sulfate) and the solvent removed in vacuo to give a crude oil. Purification by flash column chromatography (silica, ethyl acetate:hexanes 2:10) provided 3.7 g (76%) of methyl 4-(1H-benzimidazol-1-yl)benzoate as a white solid. To a solution of methyl 4-(1H-benzimidazol-1-yl)benzoate (3.7 g, 14.7 mmol) dissolved in THF/MeOH (1:1, 90 mL) was added 1.0 M aqueous NaOH (0.587 g, 14.67 mmol) and the reaction mixture was allowed to stir for 12 h at room temperature and the solvent removed in vacuo. The residue was diluted with water (100 mL), cooled to 0° C., and the pH was adjusted to 6.0 with 1.0 N aqueous HCl. The resulting precipitate was filtered and dried to afford 3.4 g (96%) of 4-(1H-benzimidazol-1-yl)benzoic acid as a white solid. MS [239.0 m/e (M+H)].

Example 2

Preparation of 1'-[4-1H-benzimidazol-1-yl)benzoyl]-1,3'-bipyrrolidine hydrochloride

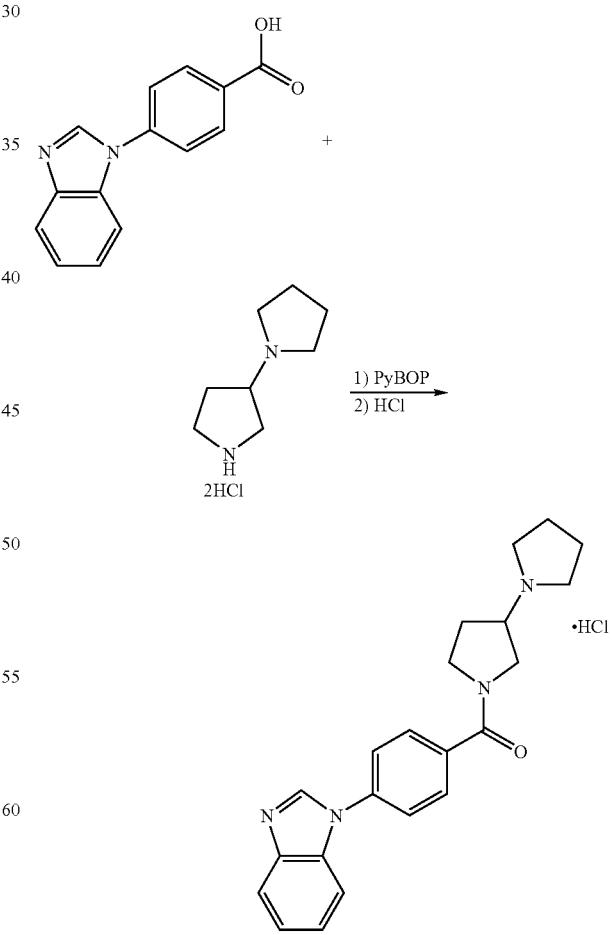

A stirred mixture of the dihydrochloride salt of 3-(pyrrolidino)pyrrolidine (0.44 g, 2.1 mmol) and 4-(1H-benzimidazol-1-yl)benzoic acid (0.38 g, 1.6 mmol) in $CH_2Cl_2$ is treated with 0.85 mL of triethylamine at room temperature. The reaction mixture is treated with solid benzotriazol-1-yl-oxytripyrrolidinophosphonium hexafluorophosphate (PyBOP) (1.2 g, 2.4 mmol), stirred overnight under nitrogen, diluted with $CH_2Cl_2$, washed sequentially with water and brine, dried over $MgSO_4$ and concentrated in vacuo. The resultant residue is chromatographed. The chromatographed material is treated with HCl in ether to afford the title compound as a white solid, identified by NMR and mass spectral analyses. MS (ES) m/z 361.4 (M+H)

dichloromethane, washed sequentially with water and saturated NaCl, dried over $MgSO_4$ and concentrated in vacuo to give a crude oil. Purification of this oil by flash column chromatography (silica, methanol:$CH_2Cl_2$ 5:95) provides the title product as a white solid, 2.38 g (64% yield), identified by NMR and mass spectral analyses. (MS [308.4 m/e (M+H)].

Example 4

Preparation of (3R)-1-[4-(1H-benzimidazol-1-yl)benzoyl]pyrrolidin-3-yl methane-sulfonate Example 3

Preparation of (3R)-1-[4-(1H-benzimidazol-1-yl)benzoyl]pyrrolidin-3-ol

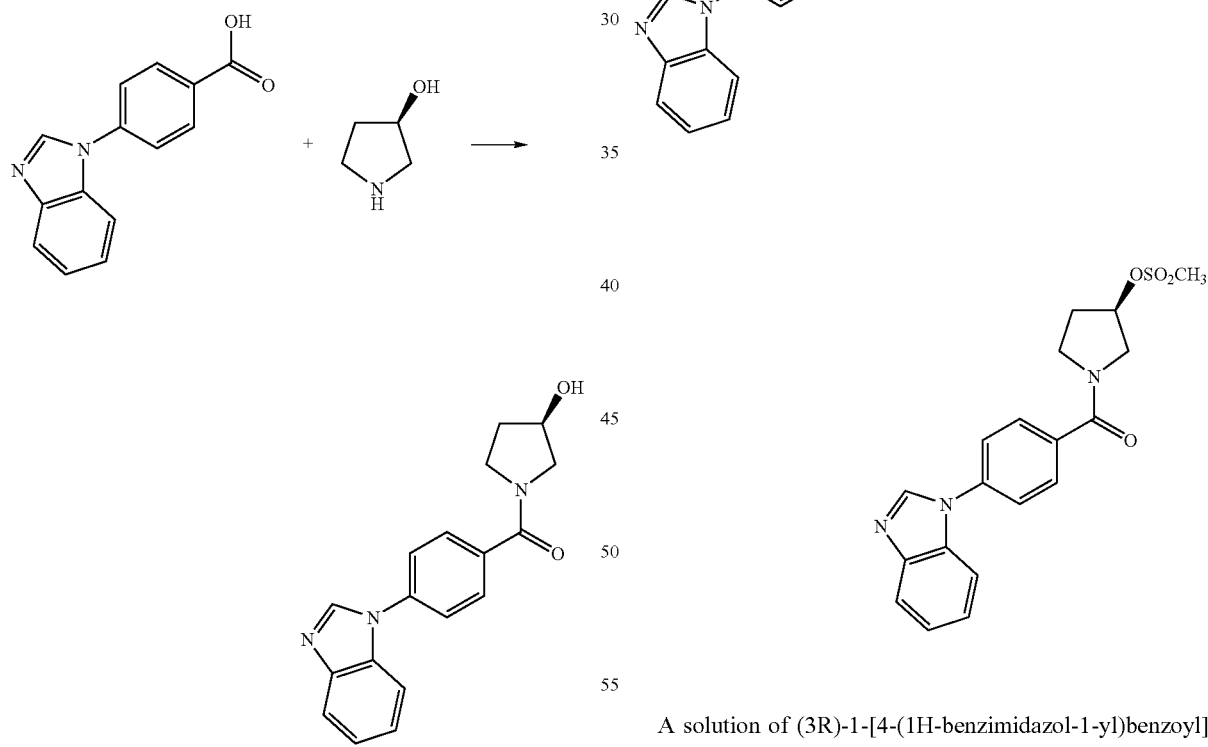

A solution of 4-(1H-benzimidazol-1-yl)benzoic acid (2.88 g, 12.09 mmol) in DMF is treated with (3R)-pyrrolidin-3-ol (1.106 g, 12.69 mmol), 1-ethyl-3(3-dimethylaminopropyl)carbodiimide (2.78 g, 14.51 mmol) and N-hydroxybenzotriazole (1.89, 13.29 mmol), stirred at 80° C. for 12 hours and concentrated in vacuo. The resultant residue is dissolved in A solution of (3R)-1-[4-(1H-benzimidazol-1-yl)benzoyl]pyrrolidin-3-ol (2.30 g, 7.48 mmol) in anhydrous dichloromethane at 0° C. is treated with diisopropylethyl amine (2.13 g, 16.46 mmol) and methanesulfonyl chloride (1.29 g, 11.22 mmol), stirred at 0° C. for 2 hours and concentrated to give a crude oil. Purification of this oil by flash column chromatography (silica, methanol:dichloromethane 5:95) provides the title product as a yellow solid, 2.3 g (81% yield), identified by NMR and mass spectral analyses. MS [386.5 m/e (M+H)].

Example 5

Preparation of (3'S)-1'-[4-(1H-benzimidazol-1-yl)benzoyl]-1,3'-bipyrrolidine hydrochloride

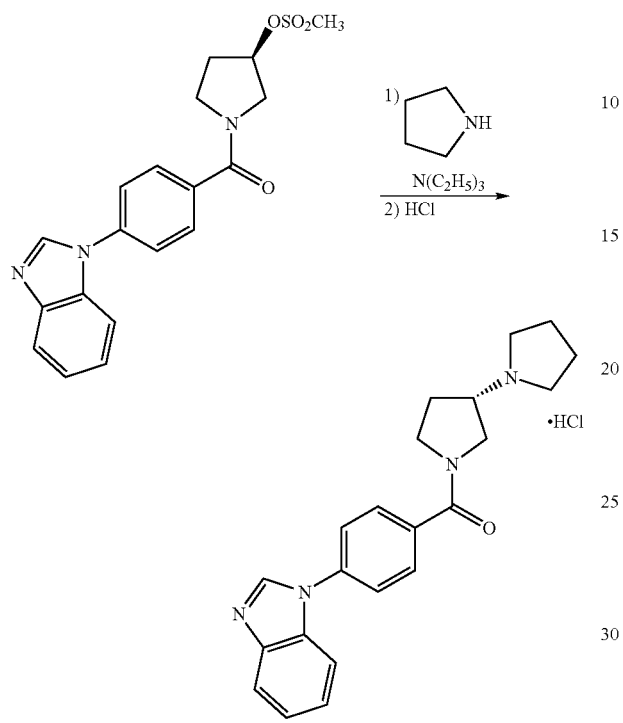

A solution of (3R)-1-[4-(1H-benzimidazol-1-yl)benzoyl]pyrrolidin-3-yl methanesulfonate (0.180 g, 0.467 mmol) in anhydrous acetonitrile is treated with pyrrolidine (0.332 g, 4.67 mmol) and triethylamine (0.094 g, 0.934 mmol), heated to 180° C. via microwave radiation for 30 minutes. The reaction mixture is concentrated to give a crude oil. Purification of this oil by flash column chromatography (silica, methanol:dichloromethane 1:9), followed by treatment with ethereal HCl, affords the title product as a yellow solid, 0.147 g (79% yield), identified by NMR and mass spectral analyses. MS [361.1 m/e (M+H)].

Examples 6-13

Preparation of 1-(4-{[(3S)-[3-amino-pyrrolidin-1-yl]carbonyl}phenyl)-(1H-benzimidazole hydrochloride Compounds

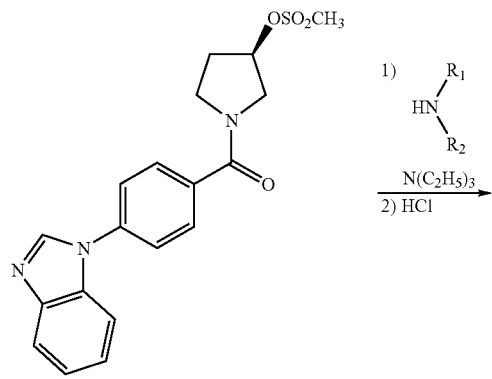

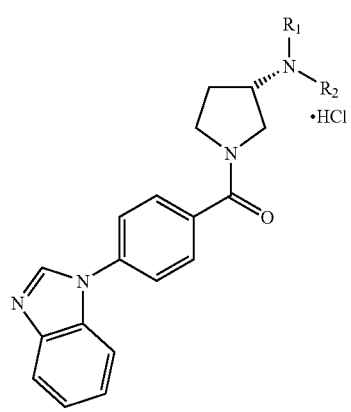

Using the sample procedure described in Example 5 and employing the appropriate amine, the compounds shown in Table I are obtained and identified by NMR and mass spectral analyses.

TABLE I

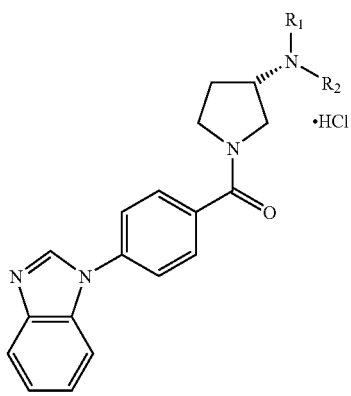

| Ex. No. | HNR1R2 | m/z [M + H] |
|---|---|---|
| 6 | (R)-2-methylpyrrolidine | 375.3 |
| 7 | (S)-2-methylpyrrolidine | 375.3 |
| 8 | 3-methylpiperidine | 389.3 |
| 9 | 4-methylpiperidine | 389.3 |
| 10 | 4-methylpiperazine | 390.3 |
| 11 | azepane | 389.3 |
| 12 | 2-methylpiperidine | 389.0 |
| 13 | piperidine | 375.2 |

Example 14

Preparation of (3'S)-1'-[4-(1H-benzimidazol-1-yl)benzyl]-1,3'-bipyrrolidine hydrochloride

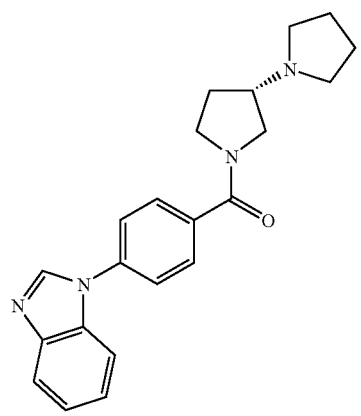

A solution of (3'S)-1'-[4-(1H-benzimidazol-1-yl)benzoyl]-1,3'-bipyrrolidine (0.041 g, 0.113 mmol) in THF is treated with 1.0 M Borane-THF (0.098 g, 1.13 mmol) at room temperature, stirred for 12 hours and concentrated under vacuum. The resultant residue is dissolved in methanol, and treated with 1.0 M HCl-Et$_2$O (0.004 g, 0.113 mmol), heated at reflux temperature for 3 hours and concentrated under vacuum to afford an oil residue. The residue is dissolved in CH$_2$Cl$_2$, washed with saturated NaHCO$_3$ solution, dried over MgSO$_4$ and concentrated in vacuo. Purification of the concentrate by flash column chromatography (silica, 2% NH$_4$OH:MeOH:CH$_2$Cl$_2$ 5:3:95), followed by treatment with ethereal HCl, provides the title product as a yellow solid, 0.036 g (65% yield), identified by NMR and mass spectral analyses. MS [347.2 m/e (M+H)].

Example 15

Preparation of (1-(4-{[(3S)-3-piperidin-1-ylpyrrolidin-1-yl]methyl}phenyl)-1H-benzimidazole fumaric acid salt

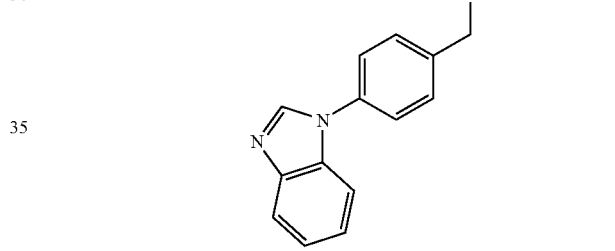

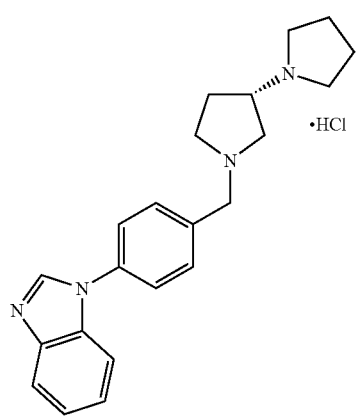

Using essentially the same procedure described in Example 14 and employing 1-(4-{[(3S)-3-piperidin-1-ylpyrrolidin-1-yl]carbonyl}phenyl)-1H-benzimidazole as starting material and fumaric acid, the title compound was obtained and identified by NMR and mass spectral analyses. MS [361.2 m/e (M+H)].

Example 16

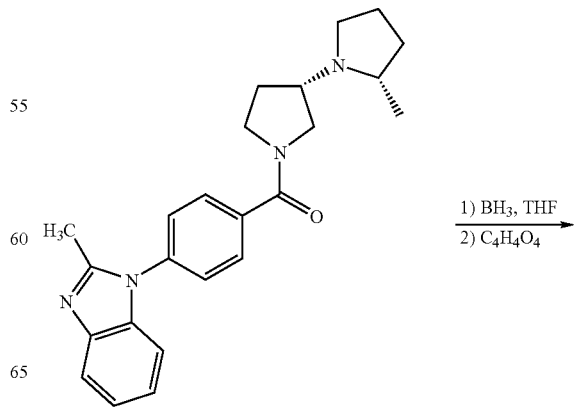

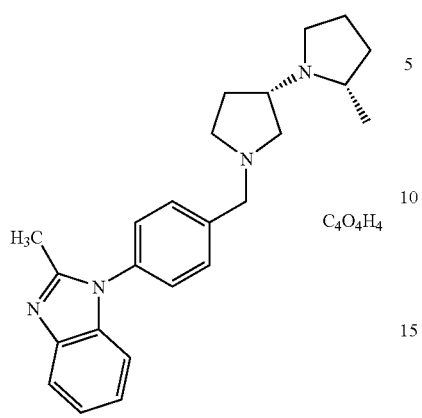

A solution of (2S,3'S)-2-methyl-1'-[4-(2-methyl-1H-benzimidazol-1-yl)benzoyl]-1,3'-bipyrrolidine (0.093 g, 0.239 mmol) in THF is treated with 1.0M Borane-THF (0.098 g, 2.39 mmol) at room temperature, stirred for 12 hours and concentrated under vacuum. The resultant residue is dissolved in methanol, and treated with 1.0 M HCl-Et$_2$O (0.004 g, 0.113 mmol), heated at reflux temperature for 3 hours and concentrated under vacuum to afford an oil residue. The residue is dissolved in CH$_2$Cl$_2$, washed with saturated NaHCO$_3$ solution, dried over MgSO$_4$ and concentrated in vacuo. Purification of the concentrate by flash column chromatography (silica, 2% NH$_4$OH:methanol:CH$_2$Cl$_2$ 5:3:95), followed by treatment with fumaric acid, provides the title product as a yellow solid, 0.034 g (38% yield), identified by NMR and mass spectral analyses. MS [375.2 m/e (M+H)].

Examples 17-18

Preparation of (1-(4-{[(3S)-3-amino-pyrrolidin-1-yl]methyl}phenyl)-1H-benzimidazole fumaric acid salt Compounds Using the same procedure described in Example 16 and employing the appropriate amine, the compounds shown in Table II are obtained and identified by NMR and mass spectral analyses.

TABLE II

| Ex. No. | HNR1R2 | m/z [M + H] |
|---|---|---|
| 17 | pyrrolidine | 361.2 |
| 18 | azepane | 389.2 |

Example 19

Preparation of (3R)-1-[4-(2-methyl-1H-benzimidazol-1-yl)benzoyl]pyrrolidin-3-yl methanesulfonate

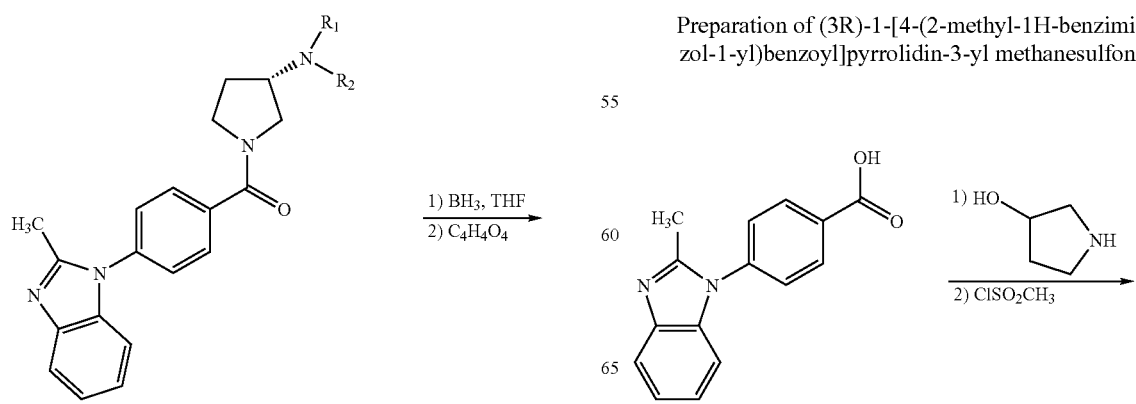

-continued

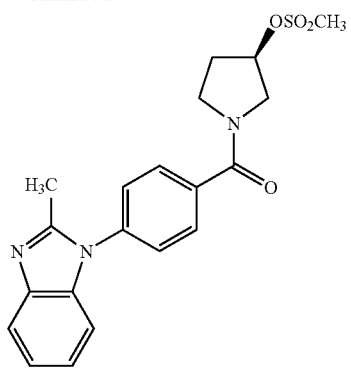

Using essentially the same procedures described in Examples 1-4 and employing 2-methyl-1H-benzimidazole as starting material, the title product is obtained as a yellow solid, identified by NMR and mass spectral analyses. MS [400.1 m/e (M+H)].

Example 20

Preparation of 1-(4-{[(3S)-3-azepan-1-ylpyrrolidin-1-yl]carbonyl}phenyl)-2-methyl-1H-benzimidazole fumaric acid salt

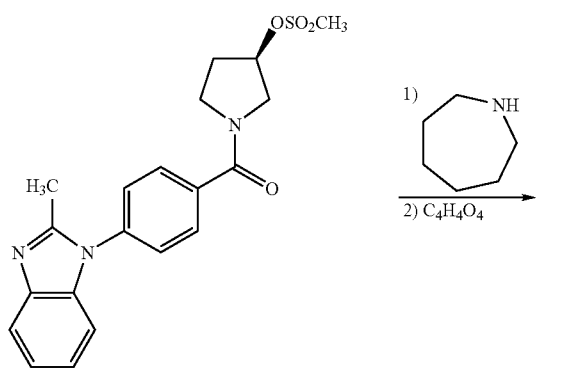

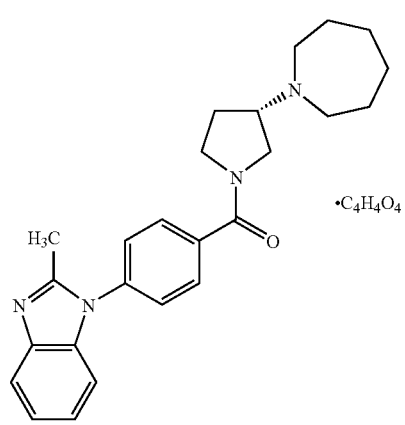

A solution of (3R)-1-[4-(2-methyl-1H-benzimidazol-1-yl)benzoyl]pyrrolidin-3-yl methanesulfonate (0.100 g, 0.250 mmol) in anhydrous acetonitrile is treated with azepane (0.248 g, 2.5 mmol) and triethylamine (0.051 g, 0.5 mmol), heated to 180° C. via microwave irradiation for 10 minutes. The reaction mixture is concentrated to give a crude oil. Purification of the oil by flash column chromatography (silica, methanol:dichloromethane 1:9), followed by treatment with fumaric acid, affords the title product as a yellow solid, 0.054 g (54% yield), identified by NMR and mass spectral analyses. MS [403.3 m/e (M+H)].

Examples 21-28

Preparation of 1-(4-{[(3S)-3-amino-pyrrolidin-1-yl]carbonyl}phenyl)-2-methyl-1H-benzimidazole fumaric acid salt

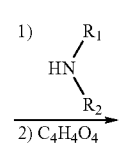

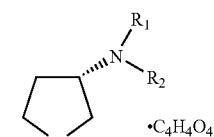

Using essentially the same procedure described in Example 19 and employing the requisite amine, the compounds shown in Table III were obtained and identified by NMR and mass spectral analyses.

TABLE III

[Structure with R1, R2 substituents on pyrrolidine-benzoyl-methylbenzimidazole · C4H4O4]

| Ex. No. | HNR1R2 | m/z [M + H] |
|---|---|---|
| 21 | (R)-2-methylpyrrolidine | 389.0 |
| 22 | (S)-2-methylpyrrolidine | 389.0 |
| 23 | 2-methylpiperidine | 403.0 |
| 24 | 3-methylpiperidine | 403.0 |
| 25 | 4-methylpiperidine | 403.0 |
| 26 | 4-methylpiperazine | 404.2 |
| 27 | pyrrolidine | 375.4 |
| 28 | piperidine | 375.4 |

Example 29

Preparation of (S)-1,3'-bipyrrolidin-1'-yl(4-fluorophenyl)methanone

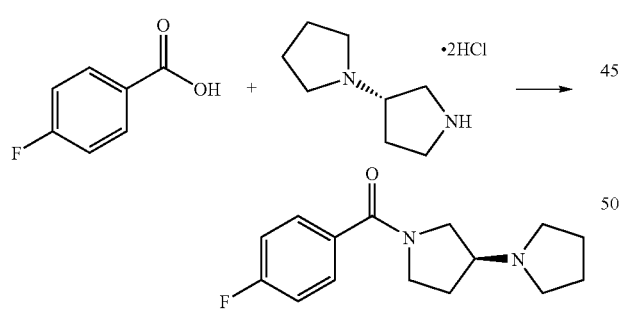

A solution of 4-fluorobenzoic acid (3.5 g, 24.98 mmol) in DMF is treated with (S)-1,3'-bipyrrolidine dihydrochloride (10.65 g, 49.96 mmol), triethylamine (12.64 g, 124.90 mmol), 1-ethyl-3(3-dimethylaminopropyl)carbodiimide (5.75 g, 28.98 mmol) and N-hydroxybenzotriazole (4.05 g, 29.98 mmol), stirred at room temperature for 16 h and concentrated in vacuo. The resultant residue is partioned between $CH_2Cl_2$ and $H_2O$. The organic phase is separated, washed sequentially with saturated $NaHCO_3$ and brine, dried over $MgSO_4$ and concentrated. The concentrate is absorbed onto silica and purified by flash column chromatography (10% methanol in $CH_2Cl_2$) to give the title product, identified by NMR and mass spectral analyses.

Example 30

Preparation of (3'S)-1'-[4-(1H-indol-1-yl)benzoyl]-1,3'-bipyrrolidine hydrochloride

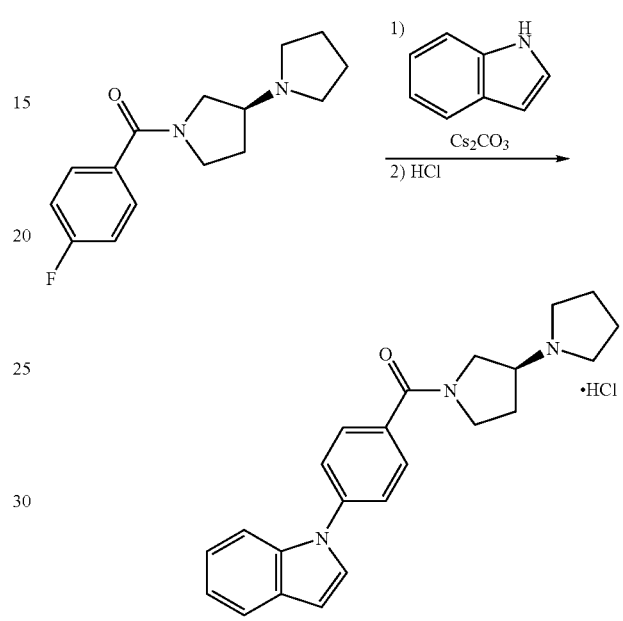

A solution of (S)-1,3'-bipyrrolidin-1'-yl(4-fluorophenyl)methanone (0.060 g, 0.23 mmol), indole (0.0269 g, 0.23 mmol), and cesium carbonate (0.0945 g, 0.29 mmol) in THF is heated in a sealed tube at 160° C. for 16 h. The reaction mixture is concentrated in vacuo. The resultant residue is partitioned between $CH_2Cl_2$ and water. The $CH_2Cl_2$ phase is separated, dried over $MgSO_4$ and concentrated in vacuo. The concentrate is purified by HPLC, followed by treatment with ethereal HCl to yield the title product as a brown solid, identified by NMR and mass spectral analyses. MS [M+H] 360.2.

Examples 31-39

Preparation of (3'S)-1'-[4-(1H-indol-1-yl)benzoyl]-1,3'-bipyrrolidine hydrochloride Compounds

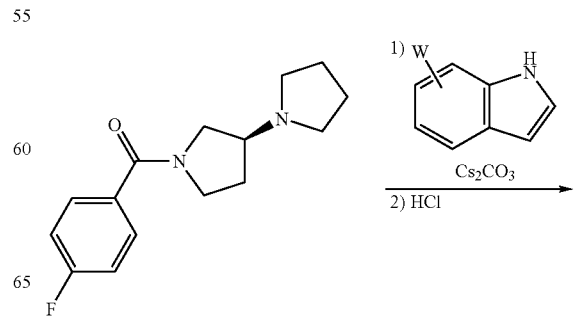

-continued

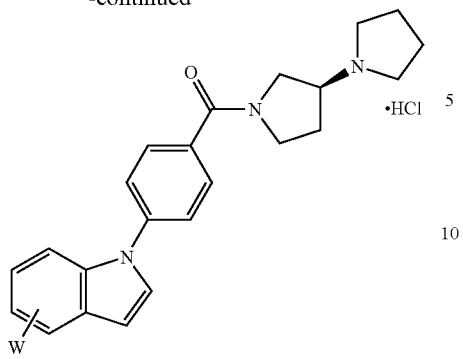

Using essentially the same procedure described in Example 30 and employing the appropriate 1H-indole, the compounds shown in Table IV are obtained and identified by NMR and mass spectral analyses.

TABLE IV

| Ex. No. | W | m/z [M + H] |
|---|---|---|
| 31 | 4-fluoro | 378.2 |
| 32 | 4-chloro | 394.2 |
| 33 | 5-methoxy | 390.2 |
| 34 | 7-chloro | 394.2 |
| 35 | 5-bromo | 438.1 |
| 36 | 5-cyano | 385.2 |
| 37 | 5-fluoro | 378.2 |
| 38 | 2-methyl | 374.2 |
| 39 | 7-fluoro | 378.2 |

Examples 40-45

Preparation of (3'S)-1'-[4-(indazolyl)benzoyl]-1,3'-bipyrrolidine hydrochloride Compounds

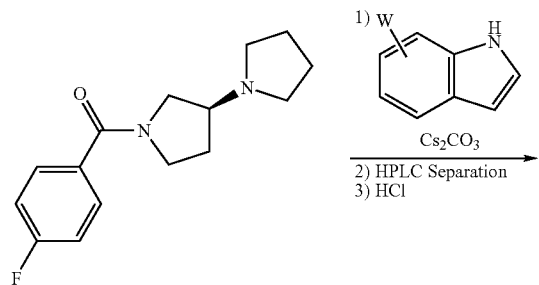

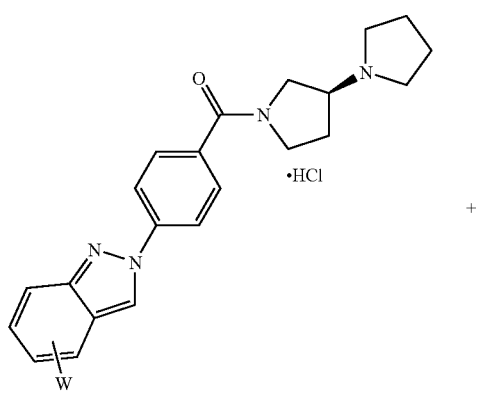

Using essentially the same procedure described in Example 30 and employing the appropriate indazole, following HPLC separation of the constitutional isomers, the compounds shown in Table V and VI are obtained and identified by NMR and mass spectral analyses.

TABLE V

| Ex. No. | W | m/z [M + H] |
|---|---|---|
| 40 | 5-fluoro | 379.2 |
| 41 | 6-fluoro | 379.2 |
| 42 | 5-cyano | 386.2 |

TABLE VI

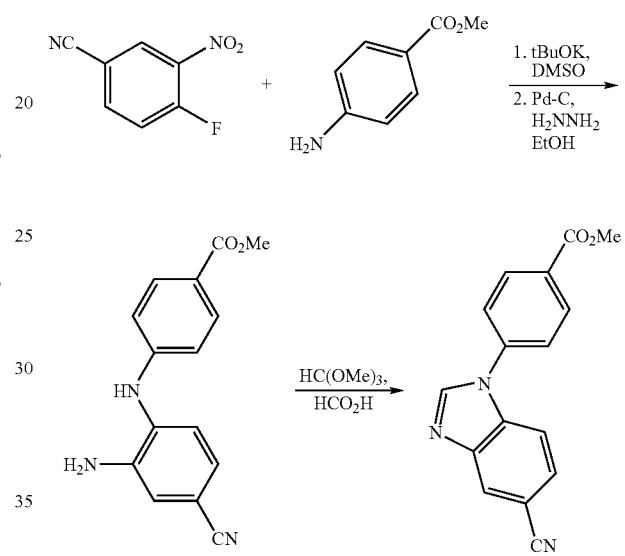

| Ex. No. | W | m/z [M + H] |
|---|---|---|
| 43 | 5-cyano | 386.2 |
| 44 | 6-fluoro | 379.2 |
| 45 | 5-fluoro | 379.2 |

Example 46

Preparation of 1-{4-[(3'R)-1,3'-bipyrrolidin-1'-ylcarbonyl]phenyl}-1H-indole-5-carbonitrile

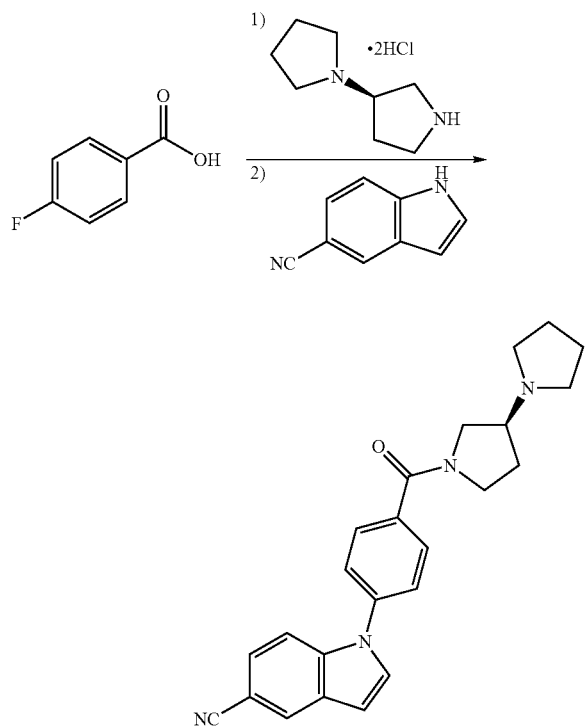

Using essentially the same procedures described in Examples 29 and 30 employing (R)-1,3'-bipyrrolidine dihydrochloride and 1H-indole-5-carbonitrile, the title compound is obtained and identified by NMR and mass spectral analyses.

Example 47

Preparation of Methyl 4-(5-cyano-1H-benzimidazol-1-yl)benzoate

A mixture of 4-fluoro-3-nitrobenzonitrile (2.00 g, 12.04 mmol) and methyl 4-aminobenzoate (1.94 g, 12.83 mmol) in DMSO (40 mL) was cooled in an ice-bath and potassium tert-butoxide (2.96 g, 26.38 mmol) was added over 15 min. The reaction mixture was allowed to stir at room temperature for 3 h. The reaction mixture was quenched with ice; the solid product was recovered by filtration, washed with water and dried under vacuum to afford 2.4 g (68%) of methyl 4-[(4-cyano-2-nitrophenyl)amino]benzoate. To a solution of methyl 4-[(4-cyano-2-nitrophenyl)amino]benzoate (0.2 g, 0.67 mmol) in ethanol (4 mL) was added palladium on carbon (10 wt. %, 0.06 g) and hydrazine hydrate (0.13 g, 2.60 mmol) and the reaction mixture was heated at reflux for 2 h. The reaction mixture was cooled to room temperature, filtered through celite, and the solvent evaporated. The residue was dissolved in ethyl acetate, washed with water, dried (Na₂SO₄) and evaporated under reduced pressure to afford a crude oil. To a solution of the oil in trimethyl orthoformate (10 mL) was added formic acid (0.31 g, 7.7 mmol, 3 eq) and the reaction mixture was heated at reflux for 2 h. The reaction mixture was cooled to room temperature and the solvent was evaporated under reduced pressure. The residue was partitioned between water and ethyl acetate and the organic layer was dried (Na₂SO₄) and evaporated to afford a crude solid. Purification by flash column chromatography (silica, CHCl₃/MeOH 98:2)

afforded 0.12 g (63%) of methyl 4-(5-cyano-1H-benzimidazol-1-yl)benzoate. MS [M+H] 277.

Example 48

Preparation of 1-{4-[(3'S)-1,3'-bipyrrolidin-1'-ylcarbonyl]phenyl}-1H-benzimidazole-5-carbonitrile fumarate

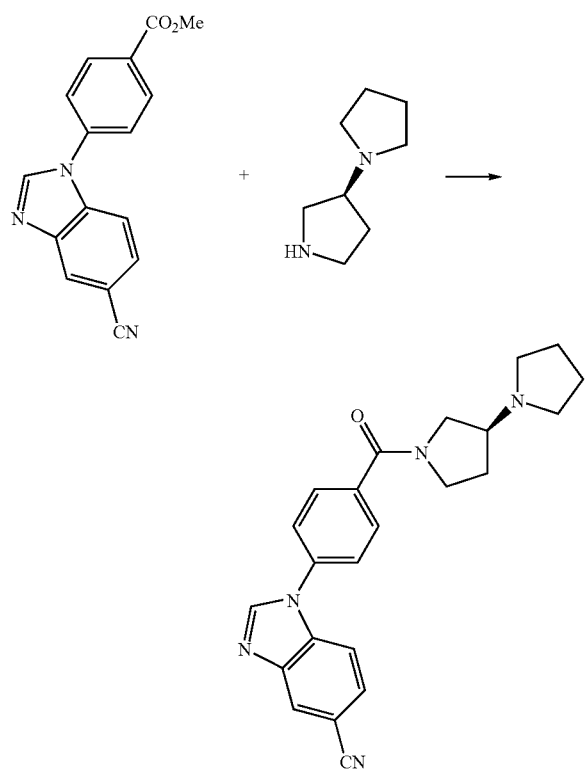

Employing methyl 4-(5-cyano-1H-benzimidazol-1-yl)benzoate and following essentially the same procedures described in Example 1 (METHOD B) for hydrolysis of the benzoic ester and Example 28 for coupling the (S)-1,3'-bipyrrolidine dihydrochloride, followed by conversion to the fumarate salt, the title compound was obtained as a white solid, identified by NMR and mass spectral analyses. MS [M+H] 386.05.

Example 49

Evaluation of Methyl Histamine Binding in Human Histamine H3 Receptor Cell Line

The affinity of test compounds for the histamine 3 (H3) receptor is evaluated in the following manner. Stably transfected HEK293T cells are grown in DMEM containing 10% heat inactivated FBS and G-418 (500 ug/ml). Cells are scraped from the plate, transferred to centrifuge tubes, washed one time in PBS by centrifugation in a Sorvall RT7 Plus centrifuge (2000 rpm 10 minutes, 4° C.). The resulting pellets are stored at −80° C. until ready for use. Cells are re-suspended in buffer (50 mM Tris pH=7.5) and placed in a Dounce homogenizer, douncing ten times to homogenize cells. The homogenate is spun down by centrifugation (Sorvall RT7 Plus, 1800 rpm 10 minutes, 4° C.). The supernatant is placed in a Corex tube and spun down by centrifugation (Sorvall RC 5c Plus, 17,000 rpm 20 minutes, 4° C.). The pellet is resuspended in buffer (50 mM Tris, pH 7.5). Protein concentration (ug/ul) is determined using the Micro-BCA Protein Determination. The binding assay is set up in a 96 well microtiter plate in a total volume of 250 uL. Non-specific binding is determined in the presence of 10 uM clobenpropit. The final radioligand concentration is 1 nM. The test compound is serially diluted using the Beckman Biomek2000 to a final approximate range of 100 uM to 100 pM. Membranes are suspended in buffer, homogenized in 2 bursts of ten seconds using a Vitris mechanical homogenizer set at power setting 5. Ten μg of membranes are added to each well. Following a one hour incubation at 30° C., the reaction is terminated by the addition of ice cold buffer and rapid filtration with a Packard Filtermate Harvester through a GF/B filter pre-soaked with 1% PEI for one hour. The plate is dried for one hour at 37° C. and 60 μL Microscint Scintillant is added to each well. The CPM per well is measured on a Packard Top Count NXT. Ki values are determined in nM. The Ki is calculated from the $IC_{50}$ (i.e. the concentration of competing ligand which displaces 50% of the specific binding of the radioligand). CPM values are expressed as % specific binding and plotted vs compound concentration. A curve is fitted using a four-parameter logistic fit and the $IC_{50}$ value is determined. The Ki is calculated from this using the Cheng-Prusoff equation: $pKi=IC_{50}/1+(L/Kd)$ where L=concentration of free radioligand used in the assay, and Kd is the dissociation constant of the radioligand for the receptor. L is determined for each experiment by counting an aliquot of the diluted radioligand (corresponding to that added to each well) and the Kd has previously been determined under identical conditions for this cell line/radioligand.

Cyclic Amp Assay for Histamine Receptor H3 Antagonism Activity.

Stable H3 cells are maintained in tissue culture flask in DMEM with high glucose, 10% FBS, 1× pen/strep, 500 ug/ml GY18, until experiment. Culture media is removed and cells are washed twice with PBS w/Ca+2 and Mg+2 plus 500 μM IBMX. Cells are then detached by tapping on the side of the flask and resuspend in the same buffer. Two thousand cells/well are incubated with 1 μM histamine plus 10 μM forskolin plus various concentrations of compounds in a total volume of 30 μL in 96 well plates for 30 min at 30° C. Final test compound concentrations range from 10-4 M to 10-9.5 M at full log dilutions. Cyclic AMP levels are measured using HitHunter cAMP kit from Discoverx, cat#900041 according to manufacturer's instruction. Chemiluminescence signals are detected using Top Count (Packard). Cyclic AMP levels in control cells receiving 10 μM forskolin plus 100 nM histamine are considered 0%, and in cells receiving 10 uM forskolin plus 100 nM histamine plus 1 μM clobenpropit are considered 100%. Data are expressed as % control and analyzed using Prizm software. The Kb values are calculated using the following equation, $KB=EC_{50}$ or $IC_{50}/[1+(ligand/Kd)]$. The data are shown in Table VII, below.

For Table VII

TABLE VII

| Example Number | H3 Binding Ki (nM) | cAMP Kb (nM) |
|---|---|---|
| 2 | A | A |
| 5 | A | C |

TABLE VII-continued

| Example Number | H3 Binding Ki (nM) | cAMP Kb (nM) |
|---|---|---|
| 6 | B | |
| 7 | A | A |
| 8 | A | |
| 9 | E | |
| 10 | E | |
| 11 | A | A |
| 12 | C | |
| 13 | A | |
| 14 | A | |
| 15 | A | |
| 17 | A | |
| 18 | A | |
| 20 | A | |
| 21 | A | A |
| 22 | A | A |
| 23 | A | |
| 24 | A | A |
| 25 | C | |
| 26 | E | |
| 27 | A | A |
| 28 | A | A |
| 30 | A | |
| 31 | A | A |
| 32 | A | |
| 33 | A | A |
| 34 | A | |
| 35 | A | |
| 36 | A | A |
| 37 | A | A |
| 38 | A | |
| 39 | A | A |
| 40 | A | |
| 41 | B | |
| 42 | A | |
| 43 | A | |
| 44 | A | |
| 45 | A | |
| 46 | A | |
| 48 | C | |

+L6 A +32 +0 +23 +0 10 nM
+L6 B +32 +0 10.1 nM-25.0 nM
+L6 C +32 +0 25.1 nM-50.0 nM
+L6 D +32 +0 50.1 nM-100 nM
+L6 E +32 +0 +22 +0 100 nM

What is claimed is:
1. A compound of formula I

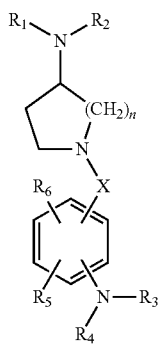

(I)

wherein
X is CO, $CH_2$ or $SO_m$;
n is an integer of 1, 2 or 3;
m is 0 or an integer of 1, or 2;
$R_1$ and $R_2$ are taken together with the atom to which they are attached to form an optionally substituted 4- to 7-membered ring optionally containing one or two additional heteroatoms selected from N, O or S
$R_3$ and $R_4$ are taken together with the atom to which they are attached to form an optionally substituted fused polycyclic 9- to 15-membered ring system optionally containing one to three additional heteroatoms selected from N, O or S;
$R_5$ and $R_6$ are each independently H, halogen, $OR_8$ or an alkyl, alkenyl, alkynyl, cycloalkyl, cycloheteroalkyl, aryl or heteroaryl group each optionally substituted;
$R_8$ is H or an optionally substituted alkyl group; or a stereoisomer thereof or a pharmaceutically acceptable salt thereof.

2. The compound according to claim 1 wherein X is CO or $CH_2$.

3. The compound according to claim 1 wherein n is 1.

4. The compound according to claim 1 wherein $R_5$ and $R_6$ are each independently H or halogen.

5. The compound according to claim 2 wherein $R_1$ and $R_2$ are taken together with the atom to which they are attached to form an optionally substituted 5-, 6- or 7-membered ring.

6. The compound according to claim 2 wherein $R_3$ and $R_4$ are taken together with the atom to which they are attached to form an optionally substituted indole, indazole, benzimidazole or carbazole ring.

7. The compound according to claim 3 wherein X is CO and $R_1$ and $R_2$ are taken together with the atom to which they are attached to form an optionally substituted 5-membered ring.

8. The compound according to claim 7 wherein $R_3$ and $R_4$ are taken together with the atom to which they are attached to form an optionally substituted indole or benzimidazole ring.

9. The compound according to claim 1 selected from the group consisting of:
1'-[4-(1H-benzimidazol-1-yl)benzoyl]-1,3'-bipyrrolidine;
(3'S)-1'-[4-(1H-benzimidazol-1-yl)benzoyl]-1,3'-bipyrrolidine;
(2R,3'S)-1'-[4-(1H-benzimidazol-1-yl)benzoyl]-2-methyl-1,3'-bipyrrolidine;
(2S,3'S)-1'-[4-(1H-benzimidazol-1-yl)benzoyl]-2-methyl-1,3'-bipyrrolidine;
1-(4-{[(3S)-3-(3-methylpiperidin-1-yl)pyrrolidin-1-yl]carbonyl}phenyl)-1H-benzimidazole;
1-(4-{[(3S)-3-(4-methylpiperidin-1-yl)pyrrolidin-1-yl]carbonyl}phenyl)-1H-benzimidazole;
1-(4-{[(3S)-3-(4-methylpiperazin-1-yl)pyrrolidin-1-yl]carbonyl}phenyl)-1H-benzimidazole;
1-(4-{[(3S)-3-azepan-1-ylpyrrolidin-1-yl]carbonyl}phenyl)-1H-benzimidazole;
1-(4-{[(3S)-3-(2-methylpiperidin-1-yl)pyrrolidin-1-yl]carbonyl}phenyl)-1H-benzimidazole;
(2R,3'S)-2-methyl-1'-[4-(2-methyl-1H-benzimidazol-1-yl)benzoyl]-1,3'-bipyrrolidine;
(2S,3'S)-2-methyl-1'-[4-(2-methyl-1H-benzimidazol-1-yl)benzoyl]-1,3'-bipyrrolidine;
2-methyl-1-(4-{[(3S)-3-(2-methylpiperidin-1-yl)pyrrolidin-1-yl]carbonyl}phenyl)-1H-benzimidazole;
2-methyl-1-(4-{[(3S)-3-(3-methylpiperidin-1-yl)pyrrolidin-1-yl]carbonyl}phenyl)-1H-benzimidazole;
2-methyl-1-(4-{[(3S)-3-(4-methylpiperidin-1-yl)pyrrolidin-1-yl]carbonyl}phenyl)-1H-benzimidazole;
2-methyl-1-(4-{[(3S)-3-(4-methylpiperidin-1-yl)pyrrolidin-1-yl]carbonyl}phenyl)-1H-benzimidazole;
2-methyl-1-(4-{[(3S)-3-(4-methylpiperazin-1-yl)pyrrolidin-1-yl]carbonyl}phenyl)-1H-benzimidazole;
(3'S)-1'-[4-(2-methyl-1H-benzimidazol-1-yl)benzoyl]-1,3'-bipyrrolidine;

2-methyl-1-(4-{[(3S)-3-piperidin-1-ylpyrrolidin-1-yl]carbonyl}phenyl)-1H-benzimidazole;

1-(4-{[(3S)-3-azepan-1-ylpyrrolidin-1-yl]carbonyl}phenyl)-2-methyl-1H-benzimidazole;

1-(4-{[(3S)-3-piperidin-1-ylpyrrolidin-1-yl]carbonyl}phenyl)-1H-benzimidazole;

(3'S)-1'-[4-(1H-benzimidazol-1-yl)benzyl]-1,3'-bipyrrolidine;

1-{4-[(3'S)-1,3'-bipyrrolidin-1'-ylcarbonyl]phenyl}-1H-indole-5-carbonitrile;

(3'S)-1'-[4-(5-bromo-1H-indol-1-yl)benzoyl]-1,3'-bipyrrolidine;

(3'S)-1'-[4-(7-chloro-1H-indol-1-yl)benzoyl]-1,3'-bipyrrolidine;

(3'S)-1'-[4-(7-fluoro-1H-indol-1-yl)benzoyl]-1,3'-bipyrrolidine;

(3'S)-1'-[4-(5-methoxy-1H-indol-1-yl)benzoyl]-1,3'-bipyrrolidine;

(3'S)-1'-[4-(4-chloro-1H-indol-1-yl)benzoyl]-1,3'-bipyrrolidine;

(3'S)-1'-[4-(2-methyl-1H-indol-1-yl)benzoyl]-1,3'-bipyrrolidine;

(3'S)-1'-[4-(4-fluoro-1H-indol-1-yl)benzoyl]-1,3'-bipyrrolidine;

1-(4-{[(3S)-3-piperidin-1-ylpyrrolidin-1-yl]methyl}phenyl)-1H-benzimidazole;

(3'S)-1'-[4-(1H-indol-1-yl)benzoyl]-1,3'-bipyrrolidine;

(3'S)-1'-[4-(5-fluoro-1H-indol-1-yl)benzoyl]-1,3'-bipyrrolidine;

(2S,3'S)-2-methyl-1'-[4-(2-methyl-1H-benzimidazol-1-yl)benzyl]-1,3'-bipyrrolidine;

(3'S)-1'-[4-(5-fluoro-2H-indazol-2-yl)benzoyl]-1,3'-bipyrrolidine;

(3'S)-1'-[4-(5-fluoro-1H-indazol-1-yl)benzoyl]-1,3'-bipyrrolidine;

1-{4-[(3'S)-1,3'-bipyrrolidin-1'-ylcarbonyl]phenyl}-1H-indazole-5-carbonitrile;

2-{4-[(3'S)-1,3'-bipyrrolidin-1'-ylcarbonyl]phenyl}-2H-indazole-5-carbonitrile;

(3'S)-1'-[4-(6-fluoro-1H-indazol-1-yl)benzoyl]-1,3'-bipyrrolidine;

(3'S)-1'-[4-(6-fluoro-2H-indazol-2-yl)benzoyl]-1,3'-bipyrrolidine;

(3'S)-1'-[4-(2-methyl-1H-benzimidazol-1-yl)benzyl]-1,3'-bipyrrolidine;

1-(4-{[(3S)-3-azepan-1-ylpyrrolidin-1-yl]methyl}phenyl)-2-methyl-1H-benzimidazole;

1-{4-[(3'S)-1,3'-bipyrrolidin-1'-ylcarbonyl]phenyl}-1H-benzimidazole-5-carbonitrile;

1-{4-[(3'R)-1,3'-bipyrrolidin-1'-ylcarbonyl]phenyl}-1H-indole-5-carbonitrile;

a stereoisomer thereof; and a pharmaceutically acceptable salt thereof.

10. A pharmaceutical composition which comprises a pharmaceutically acceptable carrier and an effective amount of a compound of formula I

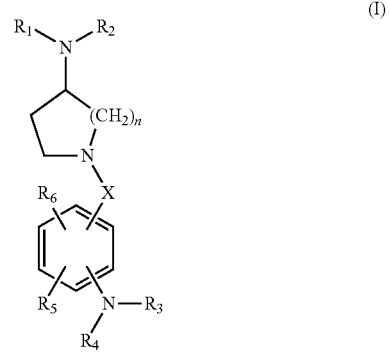

wherein

X is CO, CH$_2$ or SO$_m$;

n is an integer of 1, 2 or 3;

m is 0 or an integer of 1, or 2;

R$_1$ and R$_2$ are taken together with the atom to which they are attached to form an optionally substituted 4- to 7-membered ring optionally containing one or two additional heteroatoms selected from N, O or S R$_3$ and R$_4$ are taken together with the atom to which they are attached to form an optionally substituted fused polycyclic 9- to 15-membered ring system optionally containing one to three additional heteroatoms selected from N, O or S;

R$_5$ and R$_6$ are each independently H, halogen, OR$_8$ or an alkyl, alkenyl, alkynyl, cycloalkyl, cycloheteroalkyl, aryl or heteroaryl group each optionally substituted;

R$_8$ is H or an optionally substituted alkyl group; or a stereoisomer thereof or a pharmaceutically acceptable salt thereof.

11. The composition according to claim 10 having a formula I compound wherein X is CO or CH$_2$.

12. The composition according to claim 11 having a formula I compound wherein n is 1.

13. The composition according to claim 12 having a formula I compound wherein R$_1$ and R$_2$ are taken together with the atom to which they are attached to form a 5- or 6-membered ring and R$_3$ and R$_4$ are taken together with the atom to which they are attached to form an optionally substituted indole, indazole, benzimidazole or carbazole ring.

14. The composition according to claim 10 having a compound selected from the group consisting of:

1'-[4-(1H-benzimidazol-1-yl)benzoyl]-1,3'-bipyrrolidine;

(3'S)-1'-[4-(1H-benzimidazol-1-yl)benzoyl]-1,3'-bipyrrolidine;

(2R,3'S)-1'-[4-(1H-benzimidazol-1-yl)benzoyl]-2-methyl-1,3'-bipyrrolidine;

(2S,3'S)-1'-[4-(1H-benzimidazol-1-yl)benzoyl]-2-methyl-1,3'-bipyrrolidine;

1-(4-{[(3S)-3-(3-methylpiperidin-1-yl)pyrrolidin-1-yl]carbonyl}phenyl)-1H-benzimidazole;

1-(4-{[(3S)-3-(4-methylpiperidin-1-yl)pyrrolidin-1-yl]carbonyl}phenyl)-1H-benzimidazole;

1-(4-{[(3S)-3-(4-methylpiperazin-1-yl)pyrrolidin-1-yl]carbonyl}phenyl)-1H-benzimidazole;

1-(4-{[(3S)-3-azepan-1-ylpyrrolidin-1-yl]carbonyl}phenyl)-1H-benzimidazole;

1-(4-{[(3S)-3-(2-methylpiperidin-1-yl)pyrrolidin-1-yl]carbonyl}phenyl)-1H-benzimidazole;

(2R,3'S)-2-methyl-1'-[4-(2-methyl-1H-benzimidazol-1-yl)benzoyl]-1,3'-bipyrrolidine;

(2S,3'S)-2-methyl-1'-[4-(2-methyl-1H-benzimidazol-1-yl)benzoyl]-1,3'-bipyrrolidine;
2-methyl-1-(4-{[(3S)-3-(2-methylpiperidin-1-yl)pyrrolidin-1-yl]carbonyl}phenyl)-1H-benzimidazole;
2-methyl-1-(4-{[(3S)-3-(3-methylpiperidin-1-yl)pyrrolidin-1-yl]carbonyl}phenyl)-1H-benzimidazole;
2-methyl-1-(4-{[(3S)-3-(4-methylpiperidin-1-yl)pyrrolidin-1-yl]carbonyl}phenyl)-1H-benzimidazole;
2-methyl-1-(4-{[(3S)-3-(4-methylpiperidin-1-yl)pyrrolidin-1-yl]carbonyl}phenyl)-1H-benzimidazole;
2-methyl-1-(4-{[(3S)-3-(4-methylpiperazin-1-yl)pyrrolidin-1-yl]carbonyl}phenyl)-1H-benzimidazole;
(3'S)-1'-[4-(2-methyl-1H-benzimidazol-1-yl)benzoyl]-1,3'-bipyrrolidine;
2-methyl-1-(4-{[(3S)-3-piperidin-1-ylpyrrolidin-1-yl]carbonyl}phenyl)-1H-benzimidazole;
1-(4-{[(3S)-3-azepan-1-ylpyrrolidin-1-yl]carbonyl}phenyl)-2-methyl-1H-benzimidazole;
1-(4-{[(3S)-3-piperidin-1-ylpyrrolidin-1-yl]carbonyl}phenyl)-1H-benzimidazole;
(3'S)-1'-[4-(1H-benzimidazol-1-yl)benzyl]-1,3'-bipyrrolidine;
1-{4-[(3'S)-1,3'-bipyrrolidin-1'-ylcarbonyl]phenyl}-1H-indole-5-carbonitrile;
(3'S)-1'-[4-(5-bromo-1H-indol-1-yl)benzoyl]-1,3'-bipyrrolidine;
(3'S)-1'-[4-(7-chloro-1H-indol-1-yl)benzoyl]-1,3'-bipyrrolidine;
(3'S)-1'-[4-(7-fluoro-1H-indol-1-yl)benzoyl]-1,3'-bipyrrolidine;
(3'S)-1'-[4-(5-methoxy-1H-indol-1-yl)benzoyl]-1,3'-bipyrrolidine;
(3'S)-1'-[4-(4-chloro-1H-indol-1-yl)benzoyl]-1,3'-bipyrrolidine;
(3'S)-1'-[4-(2-methyl-1H-indol-1-yl)benzoyl]-1,3'-bipyrrolidine;
(3'S)-1'-[4-(4-fluoro-1H-indol-1-yl)benzoyl]-1,3'-bipyrrolidine;
1-(4-{[(3S)-3-piperidin-1-ylpyrrolidin-1-yl]methyl}phenyl)-1H-benzimidazole;
(3'S)-1'-[4-(1H-indol-1-yl)benzoyl]-1,3'-bipyrrolidine;
(3'S)-1'-[4-(5-fluoro-1H-indol-1-yl)benzoyl]-1,3'-bipyrrolidine;
(2S,3'S)-2-methyl-1'-[4-(2-methyl-1H-benzimidazol-1-yl)benzyl]-1,3'-bipyrrolidine;
(3'S)-1'-[4-(5-fluoro-2H-indazol-2-yl)benzoyl]-1,3'-bipyrrolidine;
(3'S)-1'-[4-(5-fluoro-1H-indazol-1-yl)benzoyl]-1,3'-bipyrrolidine;
1-{4-[(3'S)-1,3'-bipyrrolidin-1'-ylcarbonyl]phenyl}-1H-indazole-5-carbonitrile;
2-{4-[(3'S)-1,3'-bipyrrolidin-1'-ylcarbonyl]phenyl}-2H-indazole-5-carbonitrile;
(3'S)-1'-[4-(6-fluoro-1H-indazol-1-yl)benzoyl]-1,3'-bipyrrolidine;
(3'S)-1'-[4-(6-fluoro-2H-indazol-2-yl)benzoyl]-1,3'-bipyrrolidine;
(3'S)-1'-[4-(2-methyl-1H-benzimidazol-1-yl)benzyl]-1,3'-bipyrrolidine;
1-(4-{[(3S)-3-azepan-1-ylpyrrolidin-1-yl]methyl}phenyl)-2-methyl-1H-benzimidazole;
1-{4-[(3'S)-1,3'-bipyrrolidin-1'-ylcarbonyl]phenyl}-1H-benzimidazole-5-carbonitrile;
1-{4-[(3'R)-1,3'-bipyrrolidin-1'-ylcarbonyl]phenyl}-1H-indole-5-carbonitrile;
a stereoisomer thereof; and
a pharmaceutically acceptable salt thereof.

* * * * *